United States Patent
Chin et al.

(10) Patent No.: US 7,526,342 B2
(45) Date of Patent: *Apr. 28, 2009

(54) APPARATUS FOR ENDOSCOPIC CARDIAC MAPPING AND LEAD PLACEMENT

(75) Inventors: Albert K. Chin, Palo Alto, CA (US);
John W. Davis, Sunnyvale, CA (US);
Randy W. Westlund, River Falls, WI (US)

(73) Assignee: Maquet Cardiovascular LLC, San Jose, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 10/697,906

(22) Filed: Oct. 29, 2003

(65) Prior Publication Data
US 2004/0153098 A1    Aug. 5, 2004

Related U.S. Application Data

(63) Continuation-in-part of application No. 10/174,454, filed on Jun. 17, 2002, which is a continuation-in-part of application No. 10/140,309, filed on May 6, 2002, which is a continuation-in-part of application No. 09/635,721, filed on Aug. 9, 2000.

(60) Provisional application No. 60/150,737, filed on Aug. 25, 1999, provisional application No. 60/148,130, filed on Aug. 10, 1999.

(51) Int. Cl.
*A61N 1/02* (2006.01)
*A61B 17/32* (2006.01)

(52) U.S. Cl. .................................. 607/119

(58) Field of Classification Search .......... 607/17, 607/18, 119, 127, 129, 130; 600/104–106, 600/123, 129, 154–158
See application file for complete search history.

(56) References Cited

U.S. PATENT DOCUMENTS 207,932 A    9/1878   Alvord (Continued)

FOREIGN PATENT DOCUMENTS

DE    39 42 589    12/1989

(Continued)

OTHER PUBLICATIONS

P.J. de Feyter et al., "Permanent Cardiac Pacing with Sutureless Myocardial Electrodes: Experience in First One Hundred Patients," *PACE*, vol. 3, No. 2, Mar. 1980, pp. 144-149.

(Continued)

*Primary Examiner*—Mark W Bockelman
*Assistant Examiner*—Eric D Bertram
(74) *Attorney, Agent, or Firm*—Fenwick & West LLP

(57) ABSTRACT

Apparatus and surgical methods establish temporary suction attachment to a target site on the surface of a beating heart for analyzing electrical signals or hemodynamic responses to applied signals at the target sites for enhancing the accuracy of placement of cardiac electrodes at selected sites and for enhancing accurate placement of a surgical instrument maintained in alignment with the suction attachment. A suction port on the distal end of a supporting cannula carries surface-contacting electrodes and provides suction attachment to facilitate temporary positioning of the electrodes in contact with tissue at the target site, and a clamping and release mechanism to facilitate anchoring a cardiac electrode on the moving surface of a beating heart at a selected site. Analyses of sensed signals or responses to applied signals at target sites promote epicardial mapping of a patient's heart for determining optimum sites at which to attach cardiac electrodes.

2 Claims, 22 Drawing Sheets

U.S. PATENT DOCUMENTS

| | | | |
|---|---|---|---|
| 702,789 A | 6/1902 | Gibson | |
| 1,727,495 A | 9/1929 | Wappler | |
| 1,867,624 A | 7/1932 | Hoffman | |
| 2,011,169 A | 8/1935 | Wappler | |
| 2,028,635 A | 1/1936 | Wappler | |
| 2,201,749 A | 5/1940 | Vandegrift | |
| 2,316,297 A | 4/1943 | Southerland et al. | |
| 2,868,206 A | 1/1959 | Stoesser | |
| 2,944,552 A | 7/1960 | Cannon | |
| 3,185,155 A | 5/1965 | Slaten et al. | |
| 3,338,916 A | 8/1967 | Edlich | |
| 3,357,433 A | 12/1967 | Fourestier et al. | |
| 3,763,806 A | 10/1973 | Shuffield | |
| 3,856,016 A | 12/1974 | Davis | |
| 3,870,048 A | 3/1975 | Yoon | |
| 3,877,491 A | 4/1975 | Thastrup | |
| 3,882,854 A | 5/1975 | Hulka et al. | |
| 3,920,024 A * | 11/1975 | Bowers | 607/28 |
| 3,934,115 A | 1/1976 | Peterson | |
| RE29,088 E | 12/1976 | Shaw | |
| 4,022,191 A | 5/1977 | Jamshidi | |
| 4,141,365 A | 2/1979 | Fischell et al. | |
| 4,142,528 A | 3/1979 | Whelan et al. | |
| 4,181,123 A | 1/1980 | Crosby | |
| 4,235,246 A * | 11/1980 | Weiss | 607/131 |
| 4,270,549 A | 6/1981 | Heilman | |
| 4,271,839 A | 6/1981 | Fogarty et al. | |
| 4,291,707 A | 9/1981 | Heilman et al. | |
| 4,318,410 A | 3/1982 | Chin | |
| 4,319,562 A | 3/1982 | Crosby | |
| 4,479,497 A | 10/1984 | Fogarty et al. | |
| 4,493,711 A | 1/1985 | Chin | |
| 4,526,175 A | 7/1985 | Chin et al. | |
| 4,572,548 A | 2/1986 | Porowski et al. | |
| 4,630,609 A | 12/1986 | Chin | |
| 4,662,371 A | 5/1987 | Whipple et al. | |
| 4,765,341 A | 8/1988 | Mower et al. | |
| 4,779,611 A | 10/1988 | Grooters et al. | |
| 4,784,133 A | 11/1988 | Mackin | |
| 4,863,440 A | 9/1989 | Chin | |
| 4,921,483 A | 5/1990 | Wijay et al. | |
| 4,957,477 A | 9/1990 | Lundback | |
| 4,961,738 A | 10/1990 | Mackin | |
| 4,991,578 A | 2/1991 | Cohen | |
| 5,033,477 A | 7/1991 | Chin et al. | |
| 5,071,428 A | 12/1991 | Chin et al. | |
| 5,129,394 A | 7/1992 | Mehra | |
| 5,131,905 A | 7/1992 | Grooters | |
| 5,135,501 A | 8/1992 | Cameron | |
| 5,143,082 A | 9/1992 | Kindberg et al. | |
| 5,150,706 A | 9/1992 | Cox et al. | |
| 5,163,949 A | 11/1992 | Bonutti | |
| 5,183,464 A | 2/1993 | Dubrul et al. | |
| 5,183,465 A | 2/1993 | Xanthakos et al. | |
| 5,215,521 A | 6/1993 | Cochran et al. | |
| 5,246,014 A | 9/1993 | Williams et al. | |
| 5,256,132 A | 10/1993 | Snyders | |
| 5,271,380 A | 12/1993 | Riek et al. | |
| 5,282,811 A | 2/1994 | Booker et al. | |
| 5,313,962 A * | 5/1994 | Obenchain | 128/898 |
| 5,318,589 A | 6/1994 | Lichtman | |
| 5,330,502 A | 7/1994 | Hassler et al. | |
| 5,331,975 A | 7/1994 | Bonutti | |
| 5,334,150 A | 8/1994 | Kaali | |
| 5,336,252 A * | 8/1994 | Cohen | 607/119 |
| 5,339,801 A | 8/1994 | Poloyko et al. | |
| 5,373,840 A | 12/1994 | Knighton | |
| 5,376,076 A | 12/1994 | Kaali | |
| 5,385,156 A | 1/1995 | Oliva | |
| 5,391,156 A | 2/1995 | Hildwein et al. | |
| 5,397,304 A | 3/1995 | Truckai | |
| 5,433,198 A | 7/1995 | Desai | |
| 5,437,680 A | 8/1995 | Yoon | |
| 5,453,094 A | 9/1995 | Metcalf et al. | |
| 5,464,447 A | 11/1995 | Fogarty et al. | |
| 5,482,925 A | 1/1996 | Hutsell | |
| 5,489,256 A | 2/1996 | Adair | |
| 5,490,819 A | 2/1996 | Nicholas et al. | |
| 5,496,345 A | 3/1996 | Kieturakis et al. | |
| 5,514,153 A | 5/1996 | Bonutti | |
| 5,540,711 A | 7/1996 | Kieturakis et al. | |
| 5,551,947 A | 9/1996 | Kaali | |
| 5,569,183 A | 10/1996 | Kieturakis | |
| 5,569,291 A | 10/1996 | Privitera et al. | |
| 5,569,292 A | 10/1996 | Scwemberger et al. | |
| 5,571,161 A * | 11/1996 | Starksen | 607/122 |
| 5,591,192 A | 1/1997 | Privitera et al. | |
| 5,601,576 A | 2/1997 | Garrison | |
| 5,601,589 A | 2/1997 | Fogarty et al. | |
| 5,607,441 A | 3/1997 | Sierocuk et al. | |
| 5,613,937 A | 3/1997 | Garrison et al. | |
| 5,613,947 A | 3/1997 | Chin | |
| 5,618,287 A | 4/1997 | Fogarty et al. | |
| 5,630,813 A | 5/1997 | Kieturakis | |
| 5,634,895 A | 6/1997 | Igo et al. | |
| 5,650,447 A | 7/1997 | Keefer et al. | |
| 5,653,722 A | 8/1997 | Kieturakis | |
| 5,653,726 A | 8/1997 | Kieturakis | |
| 5,667,472 A | 9/1997 | Finn et al. | |
| 5,667,520 A | 9/1997 | Bonutti | |
| 5,669,927 A | 9/1997 | Boebel et al. | |
| 5,681,278 A | 10/1997 | Igo et al. | |
| 5,685,820 A | 11/1997 | Riek et al. | |
| 5,690,648 A | 11/1997 | Fogarty et al. | |
| 5,695,504 A | 12/1997 | Gifford, III et al. | |
| 5,700,275 A | 12/1997 | Bell et al. | |
| 5,702,343 A | 12/1997 | Alferness | |
| 5,702,417 A | 12/1997 | Hermann | |
| 5,707,390 A | 1/1998 | Bonutti | |
| 5,713,950 A | 2/1998 | Cox | |
| 5,716,392 A | 2/1998 | Bourgeois et al. | |
| 5,722,977 A | 3/1998 | Wilhelmy | |
| 5,725,492 A | 3/1998 | Igo et al. | |
| 5,728,148 A | 3/1998 | Bostrom et al. | |
| 5,730,756 A | 3/1998 | Kieturakis | |
| 5,738,628 A | 4/1998 | Sierocuk et al. | |
| 5,755,764 A | 5/1998 | Schroeppel | |
| 5,755,765 A | 5/1998 | Hyde et al. | |
| 5,762,604 A | 6/1998 | Kieturakis | |
| 5,772,680 A | 6/1998 | Kieturakis et al. | |
| 5,797,946 A | 8/1998 | Chin | |
| 5,800,449 A | 9/1998 | Wales | |
| 5,810,878 A | 9/1998 | Burel et al. | |
| 5,827,216 A | 10/1998 | Igo et al. | |
| 5,860,997 A | 1/1999 | Bonutti | |
| 5,897,586 A | 4/1999 | Molina | |
| 5,900,433 A | 5/1999 | Igo et al. | |
| 5,902,331 A | 5/1999 | Bonner et al. | |
| 5,904,711 A * | 5/1999 | Flom et al. | 607/129 |
| 5,931,810 A | 8/1999 | Grabek | |
| 5,957,835 A | 9/1999 | Anderson et al. | |
| 5,957,880 A | 9/1999 | Igo et al. | |
| 5,972,010 A | 10/1999 | Taheri | |
| 5,972,013 A | 10/1999 | Schmidt | |
| 5,972,020 A * | 10/1999 | Carpentier et al. | 606/208 |
| 5,980,548 A | 11/1999 | Evans et al. | |
| 6,007,522 A | 12/1999 | Agro et al. | |
| 6,007,546 A | 12/1999 | Snow et al. | |
| 6,010,531 A | 1/2000 | Donlon et al. | |
| 6,030,406 A | 2/2000 | Davis et al. | |
| 6,036,714 A | 3/2000 | Chin | |
| 6,039,748 A | 3/2000 | Savage et al. | |
| 6,048,337 A | 4/2000 | Svedman | |
| 6,068,621 A | 5/2000 | Balceta et al. | |

| | | | |
|---|---|---|---|
| 6,077,218 A | 6/2000 | Alferness | |
| 6,080,174 A | 6/2000 | Dubrul et al. | |
| 6,085,754 A | 7/2000 | Alferness et al. | |
| 6,095,968 A | 8/2000 | Snyders | |
| 6,096,064 A * | 8/2000 | Routh | 607/9 |
| 6,102,046 A | 8/2000 | Weinstein et al. | |
| 6,126,590 A | 10/2000 | Alferness | |
| 6,132,456 A * | 10/2000 | Sommer et al. | 607/127 |
| 6,156,009 A | 12/2000 | Grabek | |
| 6,162,195 A | 12/2000 | Igo et al. | |
| 6,165,183 A | 12/2000 | Kuehn et al. | |
| 6,206,004 B1 | 3/2001 | Schmidt et al. | |
| 6,237,605 B1 | 5/2001 | Vaska et al. | |
| 6,267,763 B1 | 7/2001 | Castro | |
| 6,287,250 B1 | 9/2001 | Peng et al. | |
| 6,315,778 B1 | 11/2001 | Gambale et al. | |
| 6,322,536 B1 | 11/2001 | Rosengart et al. | |
| 6,346,074 B1 | 2/2002 | Roth | |
| 6,428,556 B1 | 8/2002 | Chin | |
| 6,461,333 B1 | 10/2002 | Frezza | |
| 6,463,332 B1 | 10/2002 | Aldrich | |
| 6,478,028 B1 | 11/2002 | Paolitto et al. | |
| 6,488,689 B1 | 12/2002 | Kaplan et al. | |
| 6,530,933 B1 | 3/2003 | Yeung et al. | |
| 6,569,082 B1 | 5/2003 | Chin | |
| 6,607,547 B1 | 8/2003 | Chin | |
| 6,612,978 B2 | 9/2003 | Lau et al. | |
| 6,689,048 B2 | 2/2004 | Vanden Hoek et al. | |
| 6,697,677 B2 | 2/2004 | Dahl et al. | |
| 6,702,732 B1 | 3/2004 | Lau et al. | |
| 6,706,052 B1 | 3/2004 | Chin | |
| 6,835,193 B2 | 12/2004 | Epstein et al. | |
| 6,851,722 B2 | 2/2005 | Chui et al. | |
| 6,889,091 B2 | 5/2005 | Hine et al. | |
| 2001/0047170 A1 | 11/2001 | Branco | |
| 2002/0035361 A1 | 3/2002 | Houser et al. | |
| 2002/0052602 A1 | 5/2002 | Wang et al. | |
| 2002/0058925 A1 | 5/2002 | Kaplan et al. | |
| 2002/0111637 A1 | 8/2002 | Kaplan et al. | |
| 2002/0173622 A1 | 11/2002 | Wettstein et al. | |
| 2002/0177207 A1 | 11/2002 | Sugiyama et al. | |
| 2003/0187461 A1 | 10/2003 | Chin | |
| 2003/0212446 A1 | 11/2003 | Kaplan et al. | |
| 2008/0045946 A1 | 2/2008 | Vaska | |

FOREIGN PATENT DOCUMENTS

| | | |
|---|---|---|
| EP | 0095727 A1 | 12/1983 |
| EP | 0 642 764 | 9/1994 |
| EP | 0791330 A2 | 8/1997 |
| FR | 1 370580 | 8/1964 |
| GB | 2 082 459 | 8/1981 |
| GB | 2 195 540 | 9/1987 |
| SU | 510235 | 4/1976 |
| SU | 1371689 | 3/1986 |
| WO | WO 96/00038 | 1/1996 |
| WO | WO 96/32882 | 10/1996 |
| WO | WO97/26831 | 7/1997 |
| WO | WO 98/24378 | 6/1998 |
| WO | WO 98/24488 A2 | 6/1998 |
| WO | WO 98/24488 A3 | 6/1998 |
| WO | WO 99/13785 | 3/1999 |
| WO | WO 99/13936 | 3/1999 |
| WO | WO 00/40159 A1 * | 7/2000 |
| WO | WO 0040159 A1 | 7/2000 |

OTHER PUBLICATIONS

S. Stewart, M.D., "Placement of the Sutureless Epicardial Pacemaker Lead by the Subxiphoid Approach," *The Annals of Thoracic Surgery*, vol. 18, No. 3, Sep. 1974, pp. 308-313.

L. Watkins, Jr., M.D. et al., "Implantation of the Automatic Defibrillator: The Subxiphoid Approach," *The Annals of Thoracic Surgery*, vol. 34, No. 5, Nov. 1982, pp. 515-520.

R. Broadman et al., "ICD Implantation via Thoracoscopy, "Mailslot" Thoracotomy and Subxiphoid Incision," *The Annals of Thoracic Surgery*, vol. 57, No. 2, Feb. 1994, pp. 475-476.

M. Zenati, M.D. et al., "Left Heart Pacing Lead Implantation Using Subxiphoid Videopericardioscopy," *J. Cardiovasc Electrophysiol*, vol. 14, Sep. 2003, pp. 949-963.

Bartoccioni, S., et al., Laparoscopic Harvesting of Right Gastroepiploic Artery for Coronary Artery Bypass Graft Performed Without Stemotomy [online], [retrieved on Oct. 5, 1999] Retrieved from the internet <URL:http://www.ctsnet.org/doc/2628.

Benetti, Federico, et al., "Video Assisted Coronary Bypass Surgery", J Card Surgery, 1995, pp. 620-625.

Bernhard, Victor M. et al., "Cardiovascular Endoscopy: Historical Perspectives", Endovascular Surgery, 1989 W.B. Saunders Company, pp. 13-30.

Carpentier, A., "Technique d'implantation de pace-maker par une voie d'abord abdominale sous-xyphoidienne," *La Presse Medicale*, Masson et Cie, Editeurs, Paris, vol. 76, No. 2, Jan. 13, 1968, 2 pp.

Comedicus Gets Approval to Sell Product in European Union, Mar. 1, 1999, Swenson NHB Investor Relations, 4 pages.

Delaria, G.A. et al., "Leg Wound Complications Associated With Coronary Revascularization", J. Thorac, Cardiovasc. Surgery, 81:403-407, 1981.

Dimitri, W.R., et al., "A Quick and Atraumatic Method of Autologous Vein Harvesting Using the Subcutaneous Extraluminal Dissector", J. Cardiovasc. Surg., 28:103-11, 1987.

Fogarty, M.D., Thomas J., et al., "Selected Applications of Ballon Dissection", pp. 45-52.

Fontenelle, Larry, J., "Subxiphoid Pericardial Window", Thoracic and Cardiovascular Surgery, The American Association for Thoracic Surgery, Jul. 1971, vol. 62, No. 1, pp. 95-97.

Grandjean, Jan G., et al., "Coronary Reoperation via Small Laparotomy Using Right Gastroepiploic Artery Without CPB", Society of Thoracic Surgeons, 1996, pp.

Hauer, G., et al. "Endoscopic Subfascial Discussion of Perforating Vein", Surg. Endos. 2:5-12, 1988.

Kaminski, Diane, "Firm Aims to Bypass Heart-piercing Treatments", Medical Industry Today, Medical Data International, Sep. 23, 1998.

"Incision Decision", Atrium Medical Corporation advertisement, appearing in J. Thorac. Cardiovasc. Surg., 83(4), 1982.

Kirklin, John W., et al., "Cardiac Surgery: Morphology, Diagnostic Criteria, Natural History, Techniques, Results, and Indications", vol. 2, Second Edition, 1993, Chapter 52, p. 1695.

Levin, Bradley H., "The Subxiphoid Pericardial Window", Surgery, Gynecology & Obstetrics, Dec. 1982, vol. 155, pp. 804-806.

Meldrum-Hanna, W. et al., "Long Saphenous Vein Harvesting," J. Surg., 56: 923-924, 1986.

Moazami, N., M.D. et al., "Minimally Invasive Greater Saphenous Vein Harvesting For Coronary Artery Bypass Surgery", Mar. 1997, pp. 94-98.

Prager, Richard L., et al., "The Subxiphoid Approach to Pericardial Disease", The Annals of Thoracic Surgery, vol. 34, No. 1, Jul. 1982.

Rashid, A., et al., "Subcutaneous Technique for Saphenous Vein Harvest", Ann. Thorac. Surg., 37(2):169-170, 1984.

Sabiston, David C., Jr., et al., "Atlas of Cardiothoracic Surgery", W.B. Saunders Company, 1995, pp. 235-237.

Santos, Gil H., et al., "The Subxiphoid Approach in the Treatment of Pericardial Effusion", Albert Einstein College of Medicine, Sep. 21, 1976, pp. 467-470.

"Saphenous Vein Grafts Are No. 1, Period," Atrium Medical Corporation advertisement, appearing in J. Thorac. Cardiovas. Surg., 82(6), 1981.

Simonsen, Michael, Ph.D., "Researchers Undaunted by Setbacks in the Angiogeneis Sector", American Health Consultants, vol. 5, No. 5, May 1999.

Spodick, David H., "Directly Applied Cardiac Therapy: Experts Explore Potential Benefits", Internal Medicine World Report, 1998.

Spodick, David H., "IPTD: Intrapericardial Therapeutics and Diagnostics: The PerDUCER Permits Direct Access to the Heart", Cath-Lab Digest, Sep. 1999, vol. 7, No. 9.

The 4th International Symposium on Intrapericardial Therapeutics and Diagnostics, Mar. 6, 1999, New Orleans, Louisiana.

Wheatley, D.J., M.D., ed., "Surgery of Coronary Artery Disease", C.V. Mosby Company, pp. 348-349, pp. 374-375.

International Search Report and Written Opinion, PCT/US04/00859, Jun. 20, 2005.

International Search Report and Written Opinion, PCT/US04/00760, Jul. 6, 2005.

Myers, E. L. et al., "Tsg101, and Inactive Homologue of Ubiquitin Ligase E2, Interacts Specifically With Human Immunodeficiency Virus Type 2 Gag Polyprotein and Results in Increased Levels of Ubiquinated Gag," J. Virol, Nov. 2002, vol. 76, No. 22.

PCT International Search Report and Written Opinion; PCT/US04/34538, Nov. 3, 2005, 10 pages.

PCT International Search Report and Written Opinion, PCT/US04/00760, Sep. 27, 2006, 7 pages.

PCT International Search Report and Written Opinion, PCT/US04/22137, Jul. 9, 2007, 8 pages.

European Supplementary Search Report, EP04795673, Jan. 4, 2008, 6 pages.

* cited by examiner

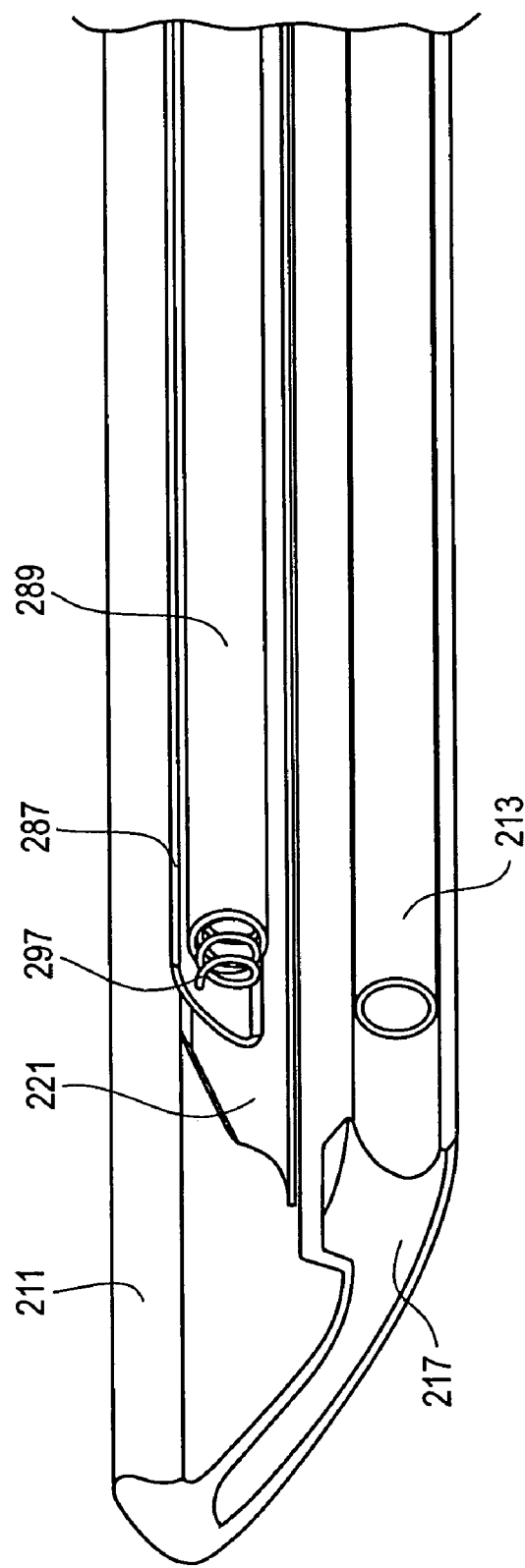

211
213
217

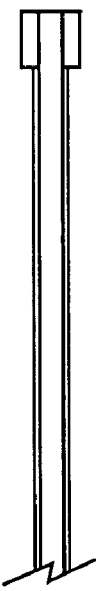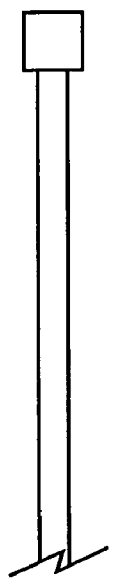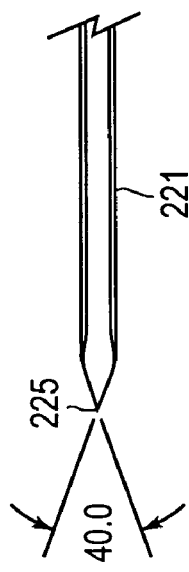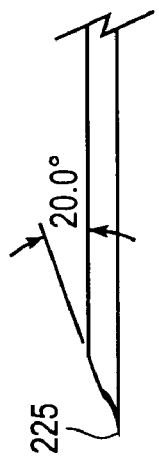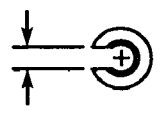
FIG. 23A
FIG. 23C
FIG. 23D
FIG. 23B

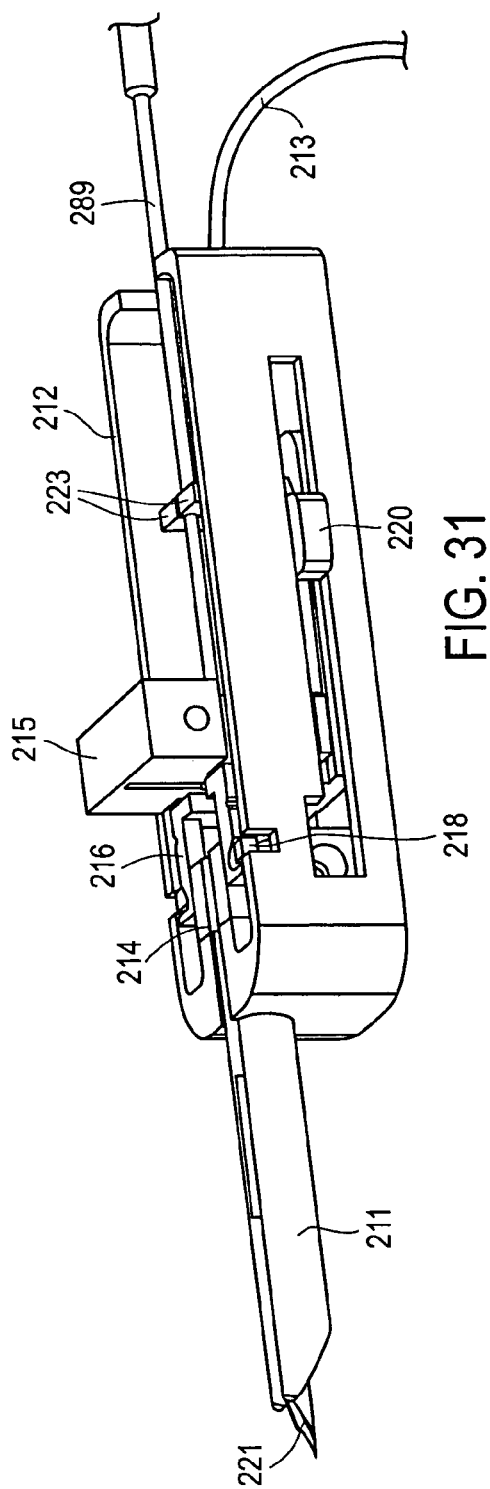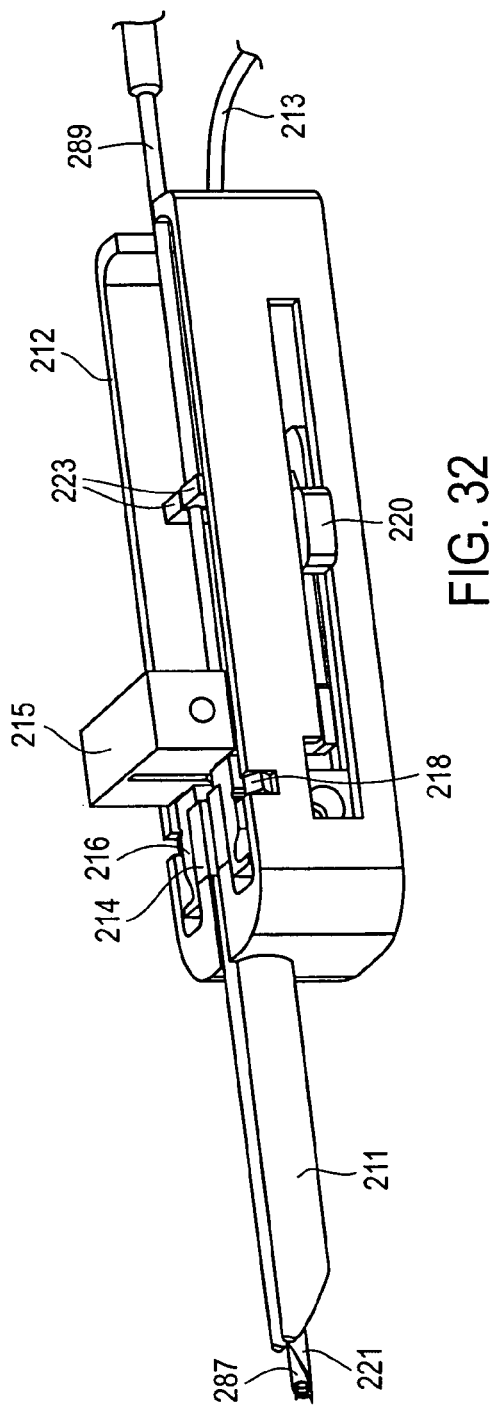

APPARATUS FOR ENDOSCOPIC CARDIAC MAPPING AND LEAD PLACEMENT

RELATED APPLICATIONS

This application is a continuation-in-part of application Ser. No. 10/174,454, entitled "Releasable Guide and Method for Endoscopic Cardiac Lead Placement" filed on Jun. 17, 2002 by A. Chin, which is a continuation-in-part of application Ser. No. 10/140,309, entitled "Methods And Apparatus For Endoscopic Cardiac Surgery", filed on May 6, 2002 by A. Chin. et al, which is a continuation-in-part of application Ser. No. 09/635,721, entitled "Apparatus for Endoscopic Access", filed on Aug. 9, 2000 by A. Chin, which claims the benefit of the filing of provisional application Nos. 60/150,737, on Aug. 25, 1999, and 60/148,130 on Aug. 10, 1999, each of which applications is incorporated herein in its entirety by this reference.

TECHNICAL FIELD

This invention relates to endoscopic cardiovascular surgical procedures and instruments, and more particularly to apparatus including a vacuum-assisted cannula and surgical instruments operable therewith, and to surgical procedures utilizing such apparatus.

BACKGROUND OF THE INVENTION

Contemporary techniques for placing cardiac electrodes at selected locations suitable for sensing and pacing the heart commonly rely upon intravascular placement of an electrode within the left ventricle. Electrode placements by such techniques are not site specific but are only generally oriented within the region of the left ventricle of the heart. More specific electrode placement within the posterior lateral aspect of the heart between the mid-portion of the ventricle and the base of the heart would be desirable, for example, for implementing cardiac resynchronization therapy (CRT) on patients that may require accurate electrode placement.

SUMMARY OF THE INVENTION

In accordance with one embodiment of the present invention, a specialized instrument is advanced through an operating channel of an endoscopic cannula to place elements in controlled manner into the wall of a beating heart. When a needle is used to form an incision for placement, sufficient control must be provided to ensure that the needle does not puncture a cardiac vein or coronary artery and cause hemorrhage within the pericardial space, with subsequent cardiac tamponade. Movement of the beating heart further complicates electrode placement because of erratic movement of the heart as sites for electrode placements are analyzed and placement of pacing electrodes on the surface of a beating heart must be carefully performed to avoid puncture of a cardiac vein or coronary artery with concomitant complications.

In accordance with the illustrated embodiments of the present invention, a substantially rigid cannula includes separate elongated lumens extending between distal and proximal ends of the cannula to provide an instrument channel and one or more separate vacuum channels at the distal end of the cannula. The instrument channel is sized to accommodate various surgical instruments including a device to anchor cardiac leads utilizing a hollow needle for penetrating the myocardium. The needle is configured for shallow penetration to avoid puncturing into a chamber of the heart with associated complications. The needle is sized to accommodate a guide channel housing epicardial pacing or defibrillating leads. Additionally, the cannula with separate lumens or channels therethrough may be incorporated into or disposed within an instrument channel of an endoscopic cannula that houses an endoscope aligned with a distal transparent tip. This assemblage of surgical instruments may be conveniently positioned through tissue disposed between a subxiphoid incision and a surgical site on the epicardium of a beating heart, or positioned through tissue disposed between a thoracotomy incision and a surgical site on the epicardium of a beating heart. In some cases, a laterally expandable sheath may be employed to form a working cavity in tissue to facilitate the placement of the vacuum channel and instrument channel at the surgical site on the epicardium, as described in the aforecited related applications.

In another embodiment of the present invention, a guide tube carries a suction tube slidably therein and supports a lead-placing channel thereon which includes rotatable or slidable half sections that house a cardiac pacing or defibrillating lead. The lead-placing channel can be configured to enclose a cardiac lead and to release the lead along a longitudinal slot therein that results from reconfiguring the channel by sliding or rotating the half sections after placement of a distal end of the cardiac lead into the myocardium. The suction tube terminates at its distal end in a suction pod that carries unipolar or bipolar electrode contacts on its distal face for providing temporary suction attachment of the assembly and electrode contact at a selected surgical location on the epicardial surface of a beating heart. The suction pod is maneuvered along the epicardial surface of the left (or right) ventricle for sensing electrical signals that can be analyzed with respect to various parameters. Once a desired site is identified, a cardiac electrode is manipulated within the placement channel to anchor the distal end of the cardiac lead in the myocardium while the placement channel is temporarily suction-anchored to the heart via the suction pod.

In still another embodiment of the present invention, an U-shaped body carries a needle and a guide channel. The guide channel can be configured to enclose a cardiac lead and to allow placement of a distal end of the cardiac lead into the myocardium. Additionally, the guide channel can be withdrawn slightly to provide endoscopic visualization of the placement of a distal end of the cardiac lead into the myocardium. A suction port at the distal end of the U-shaped body provides temporary suction attachment of the assembly at a selected surgical location on the myocardium of a beating heart while a cardiac lead is manipulated within the guide channel to anchor the distal end of the cardiac lead to the myocardium.

BRIEF DESCRIPTION OF THE DRAWINGS

FIG. 21 is a partial cut away side view of the cardiac lead delivery device of FIGS. 20 in accordance with one embodiment of the present invention;

FIGS. 23a, b, c, and d are, respectively, top, perspective, side and end views of a needle in accordance with one embodiment of the present invention;

FIG. 31 is a perspective view of a cardiac lead delivery device with a needle advanced along a U-shaped body in accordance with one embodiment of the present invention;

FIG. 32 is a perspective view of a cardiac lead delivery device with a needle and guide channel advanced along a U-shaped body in accordance with one embodiment of the present invention;

DETAILED DESCRIPTION OF THE INVENTION

Figure 1:
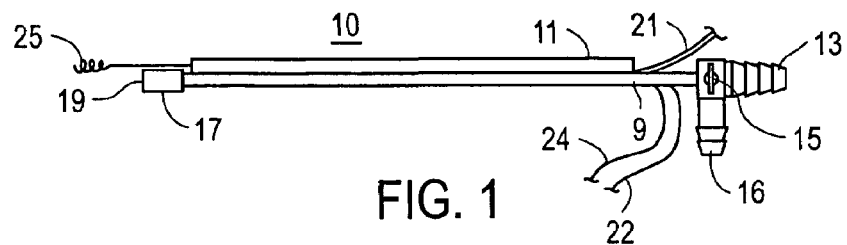
FIG. 1 is a side view of a vacuum-assisted insertion cannula in accordance with one embodiment of the present invention.
Figure 4:
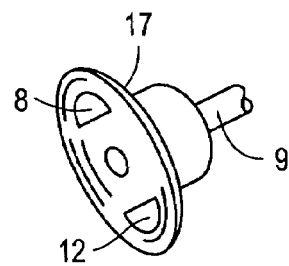
FIG. 4 is a perspective partial view of a suction cup with associated sensing and pacing electrodes positioned therein for contacting the surface of the heart.

Referring now to FIG. 1, there is shown one embodiment of a suction assisted insertion cannula 10 according to the present invention including a closed channel 9 and a superior channel 11 attached to the closed channel. The closed channel 9 includes a suitable hose connection 13 and a three-way vacuum control valve 15 including an irrigation port 16 at the proximal end. A three-way valve 15 on the cannula 9 allows suction in the pod 17 to be turned on or off, and allows irrigation fluid such as saline to be injected through the suction pod 17 at the distal end while suction is turned off. The suction pod 17 includes a flexible, resilient suction cup with a porous distal face 19 or suction ports that serves as a vacuum port. The distal surface of the suction cup includes one or more surface electrodes 8, 12 as shown in FIG. 4, for contacting a surface of the heart. The surface electrodes 8, 12 carried by the suction cup 17 can be positioned against the epicardium to facilitate electrical contact during temporary vacuum-assisted fixation as a result of the reduced air pressure of vacuum supplied to the suction pod 17. The distal end of the superior channel 11 that is attached to the closed channel 9 may thus be held in accurate fixation in alignment with a selected surgical site on the epicardium relative to the suction fixation location of the suction pod 17 on the epicardium. Electrical conductors 22, 24 connect to the surface electrodes 8, 12 and traverse the length of the suction channel 9 to facilitate connection thereto of diagnostic equipment that analyzes electrical signals sensed by the surface electrodes 8, 12 held in contact with the epicardium.

Figure 7:
FIG. 7 is a plan view of cardiac lead with screw-in electrode at the distal tip and with attached connector at the proximal end.

The superior channel 11 is sized to accommodate slidable movement therein of a cardiac lead 21 in a configuration as shown, for example, in FIG. 7. Such cardiac lead exhibits lateral flexibility and torsional and axial rigidity over its length between the proximal end and the helical or corkscrew anchor electrode 25 at the distal end to facilitate screwing the helical anchor 25 into myocardium by rotating the proximal end of the cardiac lead 21. The superior channel 11 may be about 2-2.5 mm in diameter with an internal bore of sufficient size to accommodate a cardiac lead 21 of diameter up to approximately 2 mm in diameter.

The suction pod 17 includes a flexible, resilient suction cup 19, as shown in FIG. 4, that may be mounted in alignment with the closed channel 9 which serves as the vacuum channel, or may be mounted in skewed orientation thereto for convenient positioning of the surface electrodes 8, 12 about the epicardium. Each of the surface electrodes 8, 12 is connected to a conductor 22, 24 that extends along the vacuum channel 9 to a proximal location at which a diagnostic instrument of conventional design such as a cardiac pace/sense analyzer (PSA), for example, may be connected. Such diagnostic instrument senses the electrical signals on the surface electrodes 8, 12 operating in bipolar or unipolar mode at various locations on the epicardium to analyze various parameters such as maximum depolarization interval or maximum ventricle-to-ventricle timing for identifying a site of maximum therapeutic benefit from applied pacing signals.

Alternatively, pacing signals can be supplied to the surface electrodes via conductors 22, 24 and specific hemodynamic parameters such as degree of mitral valve regurgitation, fractional ejection volume, cardiac output, and the like, can be analyzed to identify the specific site for maximum therapeutic value derived from pacing signals applied thereto.

Such examination of the electrical signals present at various sites on the epicardium of a beating heart, or analyses of hemodynamic responses to pacing signals supplied at various sites on the epicardium, constitute epicardial mapping that promotes optimal electrical pacing therapies following a myocardial infarct, or to enhance cardiac resynchronization.

A cardiac lead implanted in the heart at a site determined by the procedure described above is extended out through a small initial incision in the patient, and the proximal end may then be tunneled subcutaneously from the initial incision to an incision in the patient's upper chest where a pacemaker or defibrillator will be located for connection to the cardiac electrode 21.

Figures 8, 9:
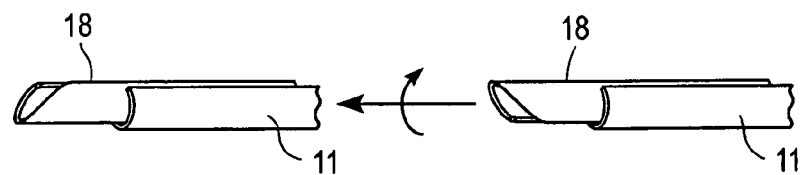
FIG. 8 is a partial plan view of an insertion cannula in one configuration incorporating an open channel for placement of a cardiac lead.
FIG. 9 is a partial plan view of the insertion cannula of FIG. 8 in a complementary configuration incorporating a closed channel.

The superior channel 11 is longitudinally slotted for placing a cardiac lead that may incorporate a large diameter connector 26, as illustrated in FIG. 7. A split sheath can be positioned around the cardiac lead 21 to facilitate advancement and rotation of the cardiac lead within the closed superior channel 11. After anchoring a cardiac lead 21 in the myocardium, for example by screwing in the distal tip 25, the slotted superior channel 11 is opened by rotating mating element 18 in the superior channel 11, as illustrated in FIGS. 8 and 9, to allow release of the cardiac lead 21 from the superior channel 11.

Figure 2:
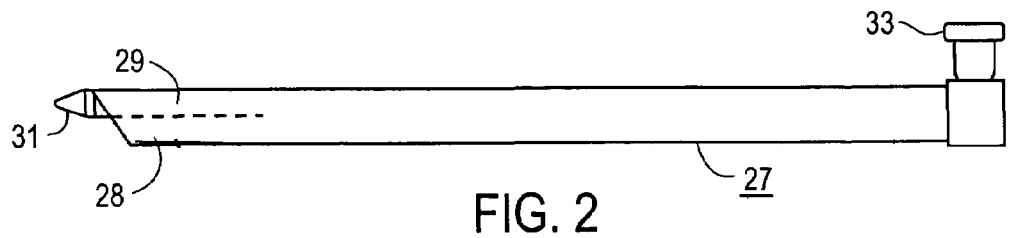
FIG. 2 is a side view of an endoscopic cannula for use with the insertion cannula of FIG. 1.
Figure 3:
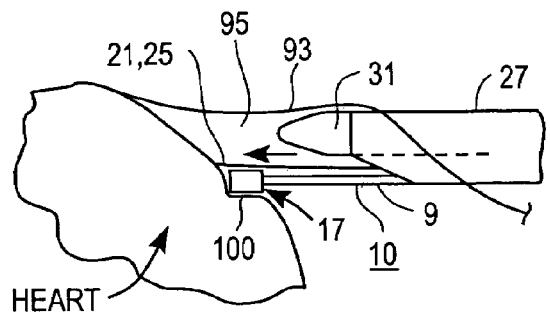
FIG. 3 is a partial side view of the assembled cannulas of FIGS. 1 and 2 in a surgical procedure.

The structure according to this embodiment of the invention, as illustrated in FIG. 1, is disposed to slide within the instrument channel 28 in an endoscopic cannula 27, as shown in FIG. 2. This cannula includes an endoscope 29 therein that extends from a tapered transparent tip 31 attached to the distal end, to a viewing port 33 at the proximal end that can be adapted to accommodate a video camera. In this configuration, the structure as illustrated in FIG. 1 may be positioned within the instrument channel in the cannula 27 of FIG. 2 to position the suction pod 17 and a distal end 25 of a cardiac lead 21 in alignment with a surgical target on the heart, as illustrated in FIG. 3. The suction pod 17 is temporarily affixed to the epicardium in response to suction applied to the porous face 19 of the suction pod 17 under control of a suction valve 15, with the surface electrodes 8, 12 carried on the distal face of the suction cup disposed in contact with epicardium at a test site. Following selection of a site for maximum therapeutic benefit in the manner as previously described, the cardiac lead 21 may then be advanced and rotated from the proximal end to anchor the distal end 25 into the myocardium at an accurately positioned surgical site, all within the visual field of the endoscope 29 through the transparent tip 31.

As illustrated in FIGS. 2 and 3, the various channels in the endoscopic cannula 27 and the insertion cannula 10 have specific orientations with respect to each other in order to provide stabilization on the epicardial surface and allow visual control of the electrode attachment process. In the endoscopic cannula 27, the instrument channel is positioned below the endoscopic channel and this allows the cannula 27 and the transparent tapered tip 31 on the endoscope 29 to retract the pericardium 93 away from the epicardial surface of the heart at the operative site. This creates a space 95 for contacting the heart below the pericardium, as illustrated in FIG. 3. As the insertion cannula 9 is advanced forward out of the instrument channel of the endoscopic cannula 27, the suction pod 17 is visualized through the endoscope 29 and transparent tip 31, as the suction pod 17 is placed on the epicardial surface of the heart. At a selected site on the heart, for example, at the site of an old myocardial infarct, the suction is activated to attach the pod 17 to the heart with the surface electrodes 8, 12 in contact with the epicardium. The configuration of the superior channel 11 of the insertion cannula 10 on top of the suction channel 9 allows the superior channel 11 and the suction pod 17 to be visible upon exiting from the instrument channel of the cannula 27, and to maintain visualization of the cardiac lead 21 within the visual field of the endoscope along the path of travel from the insertion cannula 10 to contact with the epicardium.

The configuration of the suction pod 17 with the distal surface of the suction cup oriented substantially normally to the insertion cannula 10 facilitates delivery of a cardiac electrode substantially perpendicular to the epicardial surface. In some situations, it is particularly desirable to have a cardiac electrode enter the myocardium in an orientation that is generally perpendicular to the epicardial surface for secure anchoring in the myocardium. Generally, the insertion cannula 10 is advanced through the endoscopic cannula 27 and approaches the epicardial surface of the heart at a tangential angle. Accordingly, the insertion cannula 10 may be configured to facilitate deforming the epicardial surface in order to achieve perpendicular entry of the distal end 25 of a cardiac lead 21 into the myocardium, as illustrated in FIG. 3. The suction pod 17 of the insertion cannula 10 temporarily attaches to the epicardial surface upon application of vacuum under control of the valve 15. Downward pressure can be exerted on the epicardial surface via the substantially rigid insertion cannula 10. The pliable myocardium thus deforms to create a surface ledge 100 distal to the suction pod 17 oriented perpendicular to the axis of the superior instrument channel 11 of the insertion cannula 10, as illustrated in FIG. 3. As the cardiac lead 21 is advanced, the distal end electrode 25 enters the myocardium generally perpendicularly to the epicardial surface as thus deformed for desirable lead placement.

Figure 11:
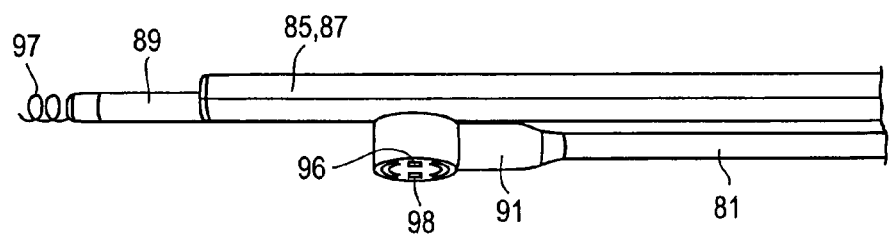
FIG. 11 is a partial plan view of the distal end of the releasable guide in the embodiment of FIG. 10.

Referring now to FIGS. 3 and 4, it should be noted that the insertion cannula 10 is sized to fit in slidable orientation within the instrument channel of about 5-7 mm diameter in the endoscopic cannula 27. The outer dimensions of the suction pod 17 are flexible and resilient for confinement in less than 5-7 mm diameter. Alternatively, the suction cup of the suction pod 17 may be skewed laterally relative to the suction channel 81, as illustrated in FIG. 11. In each embodiment, the suction channel 9, 81 is laterally displaced from the superior channel 11, 85 to avoid obstructing the forward movement of the cardiac lead 21 past the suction pod 17, 91.

Figure 5:
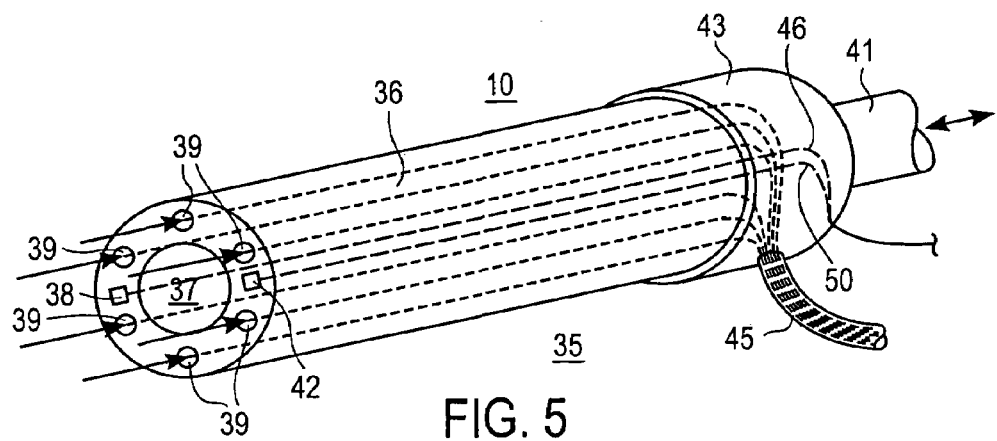
FIG. 5 is a perspective view of another embodiment of an insertion cannula in accordance with the present invention.

Referring now to FIG. 5, there is shown a perspective view of another embodiment of an insertion cannula 35 similar to insertion cannula 10 described above, including an elongated body 36 having a central bore 37, and including one or more eccentric channels 39 that serve as suction conduits. The central bore 37 may be sized to slidably support surgical instruments 41 therein such as a cardiac lead 21 disposed within a sheath, or the like. The suction pod 17 attaches to the epicardial surface while suction is applied to facilitate surface electrodes 38, 42 contacting the heart at the desired site under direct endoscopic visualization for precise cardiac mapping in response to signals sensed by the surface electrodes 38, 42 operating in bipolar or unipolar configuration.

The suction channels 39 in the cannula 35 of FIG. 5 may form a suction attachment surface at the distal end of the cannula 35, or may be disposed in fluid communication with a suitable suction pod with a porous distal face and with a central opening in alignment with the central bore 37. The suction-attaching distal face provides an opposite reaction force against a tool that exerts a pushing force such as a screw-in tip 25 of a cardiac lead 21, or other device deployed through the central bore 37 of the cannula 35. The proximal ends of the eccentric channels 39 are connected via a manifold or fluid-coupling collar 43 to a vacuum line 45, and conductors 46, 50 connected to the surface electrodes 38, 42 extend through the cannula 35 to the proximal end thereof to facilitate connection thereto of conventional diagnostic instrumentation. Alternatively, a single channel 39 may communicate with an annular recess or groove disposed concentrically about the central bore 37 within the distal end to serve as a suction-assisted attachment surface.

In this configuration, a cardiac lead 21 slidably disposed within the central bore 37 may be extended beyond the distal end of the cannula 35, within the visual field of an endoscope. The distal end 25 of the cardiac lead 21 can be oriented in alignment with a target site on the epicardium prior to supplying suction thereto to temporarily affix the cannula 35 in such position with surface electrodes 38, 42 in contact with the epicardium. A cannula 35 formed of transparent bioinert material such as polycarbonate polymer facilitates visual alignment of the cannula 35 and the surface electrodes 38, 42 with a target site, without requiring initial extension of a cardiac lead 21 forward of the distal end within the visual field of an endoscope. In an alternative embodiment, the central lumen or bore 37 may serve as a suction lumen with multiple surface electrodes 38, 42 disposed about the central bore 37.

Figure 6A:
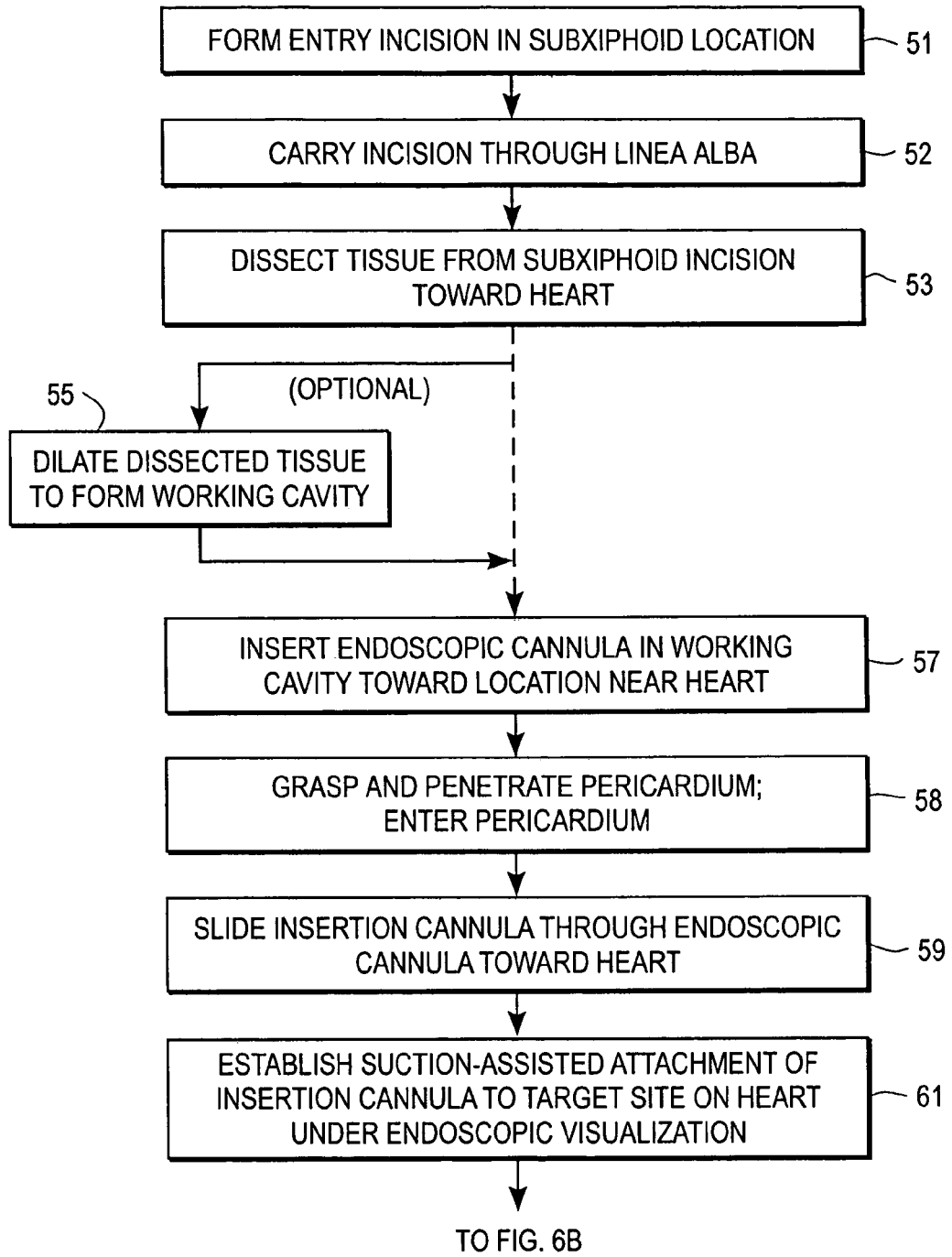
FIGS. 6a and 6b comprise a flow chart illustrating a surgical procedure in accordance with the present invention.
Figure 6B:
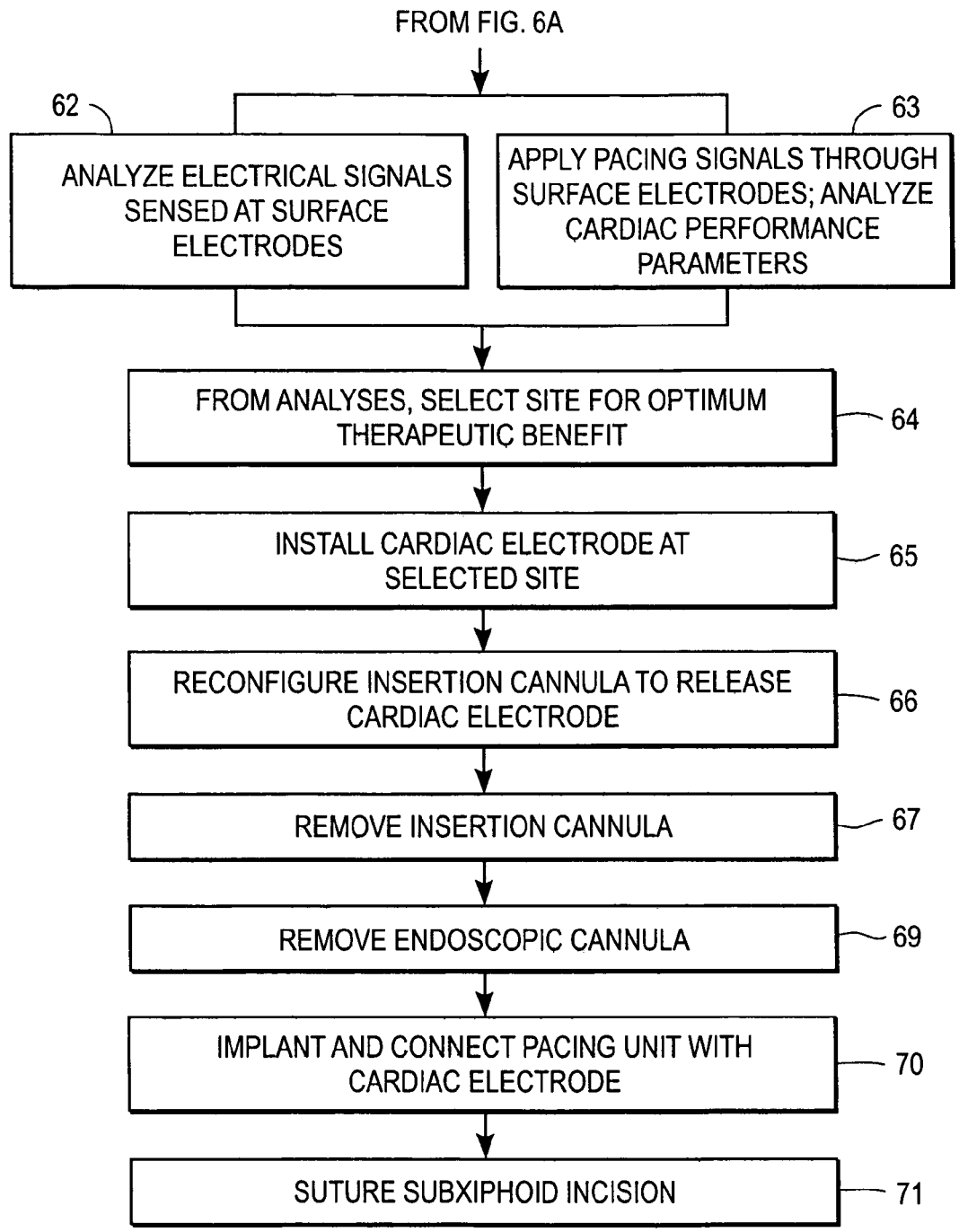

Referring now to the flow chart of FIGS. 6a, 6b, the surgical procedure for epicardially mapping the beating heart of a patient in accordance with one embodiment of the present invention proceeds from forming 51 an initial incision at a subxiphoid location on the patient. The incision is extended 52 through the midline fibrous layer (linea alba). The tissue disposed between the location of subxiphoid incision and the heart is bluntly dissected 53, for example, using a blunt-tip dissector disposed within a split-sheath cannula of the type described in the aforecited Related Applications. The channel thus formed in dissected tissue may optionally be expanded 55 by dilating tissue surrounding the channel, for example, using a balloon dilator or the split-sheath cannula referenced above, in order to form a working cavity through the dissected and dilated tissue, although this may be unnecessary.

An endoscopic cannula, for example, as illustrated in FIG. 2 including an endoscope and a lumen for receiving surgical instruments therein is inserted 57 into the working cavity through the subxiphoid incision toward the heart to provide a field of vision around a target site on the heart, and to provide convenient access via the lumen for surgical instruments of types associated with surgical procedures on the heart. One such instrument is a pericardial entry instrument, as described in the aforecited Related Applications, which generally grasps the pericardium in a side-bite manner to form an elevated ridge of tissue through which a hole can be safely formed without contacting the epicardial surface. Once the pericardium is penetrated 58, other instruments can be inserted through the hole and into the working space 58. One such instrument is an insertion cannula, for example, as illustrated in FIG. 1, that includes a suction channel and a superior channel and is slidably supported 59 within the instrument lumen of the endoscopic cannula. The suction channel of such instrument extends through the length thereof from a proximal end to a suction pod at the distal end that can be extended into contact 61 with the beating heart of the patient at a selected target site. The suction pod can be carefully positioned on the epicardium under visualization through the endoscope, and the suction can be applied to establish temporary attachment of the insertion cannula to the epicardium and to establish contact of surface electrodes with the epicardium. The electrical signals sensed on the surface electrodes may be analyzed 62 for various timing characteristics such as maximum depolarization interval or maximum (left) ventricle to (right) ventricle conduction timing, or the like. The electrical signals sensed in this manner at various sites about the heart including the posterior lateral aspect or various locations on the left ventricle of the heart, for example, with respect to a synchronizing reference event, thus facilitate selection 64 of one or more optimal sites for maximum therapeutic benefit from applied electrical pacing signals.

Alternatively, pacing signals may be applied to the epicardium via surface electrodes 38, 42 positioned at various sites about the heart in order to analyze 63 the heart's responses relative to specific hemodynamic parameters such as degree of mitral valve regurgitation, fractional ejection volume, cardiac output, and the like.

Once a site has been selected in this manner to provide maximum therapeutic benefit from applied pacing signals, a cardiac lead is installed 65 at the selected site by advancing and rotating the distal end electrode into the myocardium for good physical anchoring and electrical conduction.

The insertion cannula is then reconfigured 66 to open a longitudinal slot in the superior channel in order to release the anchored cardiac lead so that the insertion cannula can be removed 67 from the site through the instrument channel of the endoscopic cannula, leaving the cardiac electrode anchored in the myocardium at the selected site. One or more cardiac leads may be installed in this manner, after which the endoscopic cannula is also removed 69 from the working cavity. A pacing unit is then implanted 70 in the patient's chest near the clavicle, or the abdomen near the subxiphoid incision, and is connected to the one or more installed cardiac leads to deliver requisite pacing signals. The initial subxiphoid entry incision is then sutured closed 71 to conclude the surgical procedure.

The endoscopic cannula and pericardial entry instrument may also be applied from a thoracotomy incision to gain access to the heart. A 2 cm incision is performed in an intercostal space in either the left or the right chest. Ideally, the incision is made between the midclavicular line and the posterior axillary line. The incision is extended through the intercostal muscles and the pleura, until the pleural cavity is entered. The endoscopic cannula is then inserted into the pleural cavity and advanced to the desired area of entry on the contour of the heart, visualized within the pleural cavity. The pericardial entry instrument and procedure as described in the aforecited Related Applications are used to grasp the pleura, as a concentric tubular blade cuts a hole in the pleura to expose the pericardium underneath. The pericardium is then grasped by the pericardial entry instrument, and the tubular blade is used to cut a hole in the pericardium, allowing access to the heart. The transparent tapered tip 31 of the endoscopic cannula 29 aids in pleural and pericardial entry by retracting lung and pleural tissue that may impede visualization of the pericardial entry site. Once the pericardium is entered, the endoscopic cannula 29 may be moved around to visualize anterior and posterior epicardial surfaces as target sites for sensing surface electrical signals or for applying pacing signals in the manner as previously described herein.

Figure 10:
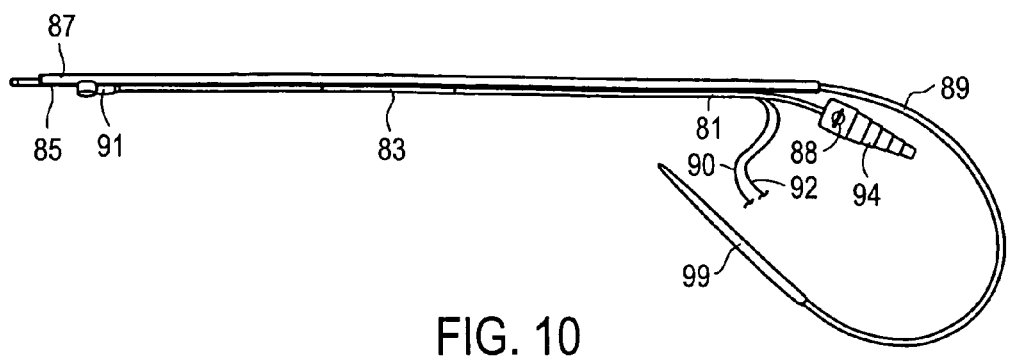
FIG. 10 is a plan view of a releasable guide for a cardiac lead according to another embodiment of the present invention.

Referring now to plan view of FIG. 10, there is shown an assembly of suction tube 81 slidably disposed within a guide tube 83 to which is mounted a lower, slotted segment 85 of a guide channel. An upper, slotted segment 87 of the guide channel is slidably or rotatably received within the lower slotted segment 85 and a cardiac pacing or defibrillating lead 89 is housed within the guide channel that is configured in the one orientation of the upper and lower segments forming closed guide channel. Another configuration of the upper and lower segments of the guide channel, as later described herein, forms an open channel or slot, as shown in FIG. 13 later described herein, for convenient release of the cardiac lead 89.

The suction tube includes a suction pod 91 at the distal end thereof and a suction-line connection fitting 94 at the proximal end for convenient hose or tubing attachment to a source of vacuum. Optionally, the connection fitting 94 may include a suction control valve 88 for adjusting the suction attachments of the suction pod to the epicardium of a patient's heart. Surface electrodes 96, 98 disposed on the tissue-contacting surface of the suction pod 91 are connected via conductors 90, 92 that extend beyond the proximal end of the assembly for attachment to diagnostic or therapeutic equipment.

The cardiac pacing or defibrillating lead 89 is slidably and rotatably housed within the guide channel 85, 87 in the closed configuration, and includes a helical or screw-in electrode 97 attached to the distal end of the cardiac lead 89, as illustrated in FIG. 11. This greatly facilitates electrically connecting and mechanically anchoring the electrode in the myocardium of a patient's beating heart at a selected site by rotating and advancing the proximal end 99 of the cardiac lead 89 within the guide channel 85, 87. For this purpose, the cardiac lead 89 exhibits high torsional and compressional rigidity and high lateral flexibility so that the electrode 97 may be accurately manipulated into screw-like attachment to the myocardium at the selected site via manual manipulation of the proximal end 99 of the cardiac lead 89. Such cardiac lead 89 may include braided multiple strands of wire coated with a layer of insulating material such as Teflon, or the like. The accuracy of placement of the screw-in electrode 97 in the myocardium of a patient's beating heart is significantly enhanced by temporary suction attachment of the suction pod 91 to the pericardium or exposed myocardium. The suction pod 91 including a flexible, resilient suction cup with one or more surface electrodes 96, 98 may be disposed in lateral or skewed orientation relative to the elongated axis of the suction tube 81. This facilitates the temporary suction attachment of the surface electrodes 96, 98 during analysis of sensed signals or hemodynamic properties of the heart. Following selection of an electrode site, the electrode 97 at the distal end of the cardiac lead 89 is slidably guided within the guide channel 85, 87 (which is disposed in skewed orientation relative to the suction pod 91 and vacuum tube 81) and is rotated to anchor the electrode 97 into the myocardium.

Figure 12:
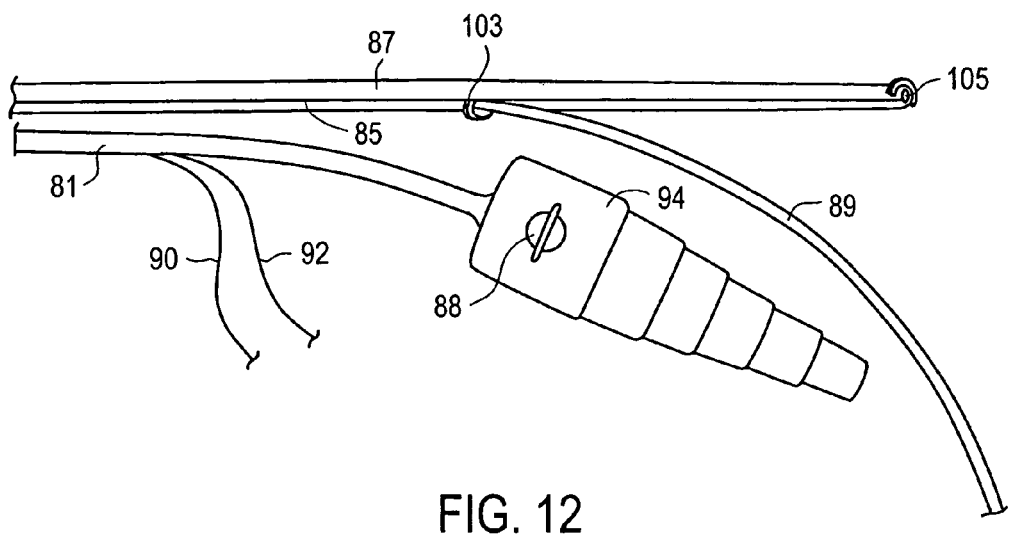
FIG. 12 is a partial plan view of the proximal end of the releasable guide in the embodiment of FIG. 10.
Figure 13:
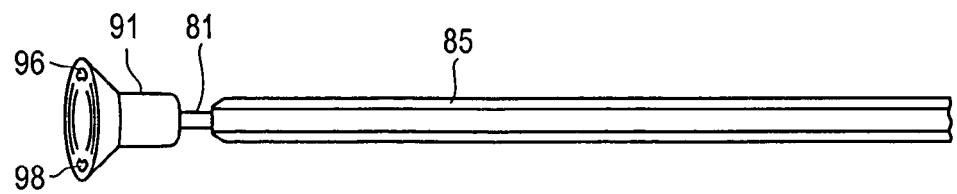
FIG. 13 is a top view of the distal end of the releasable guide in the embodiment of FIG. 10.
Figure 14:
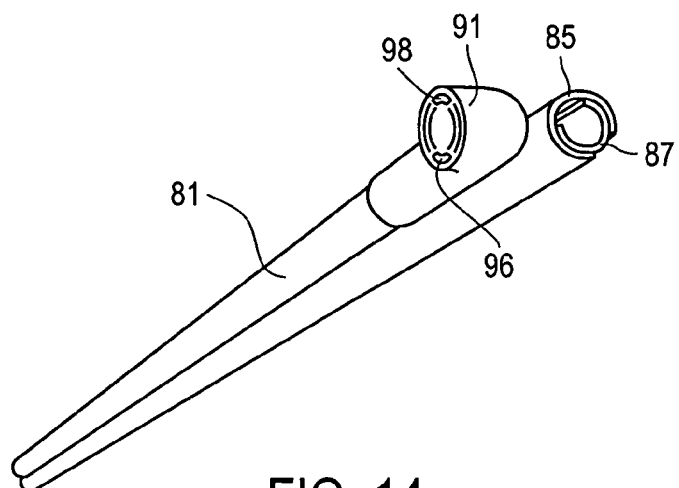
FIG. 14 is a perspective view of the distal end of the releasable guide according to the embodiment illustrated in FIG. 10.

After the electrode 97 on the distal end of the cardiac lead 89 is anchored into the myocardium of a patient's beating heart, the guide channel that houses the cardiac lead 89 may be re-configured into the alternate configuration including an open slot along the length of the guide channel, as illustrated in FIG. 13, from which the cardiac lead 89 may be easily extracted or released. This open slot configuration may be achieved by sliding the upper segment 87 proximally along the lower segment 85, as illustrated in FIG. 12, or by rotating the upper segment 87 within the lower segment 85, as illustrated in FIG. 14. In this way, a longitudinal slot or groove is opened along the entire length of the guide channel that is wide enough to extract the cardiac lead 89 therethrough. This is particularly important for anchoring a cardiac lead 89 of about 2 mm diameter that includes a proximal connector 99 which is too large to pass through a guide channel 85, 87 of reasonable interior dimension.

As illustrated in the perspective view of FIG. 14, a suction cup with surface electrodes 96, 98 disposed in suction pod 91 is oriented in skewed substantially perpendicular orientation relative to the elongated axis of the guide channel that is formed by the upper and lower segments 87, 85. This facilitates establishing temporary vacuum-assisted attachment of the suction pod 91 to the epicardium, or to myocardium exposed via the entry under the pericardium, that can then be distorted by manual application of axial or lateral force at the proximal end of the instrument in order to position one or more of the surface electrodes 96, 98 at the proper location and angle for analyzing electrical signals or hemodynamic responses to applied pacing signals at a target site on the patient's beating heart.

Figure 15:
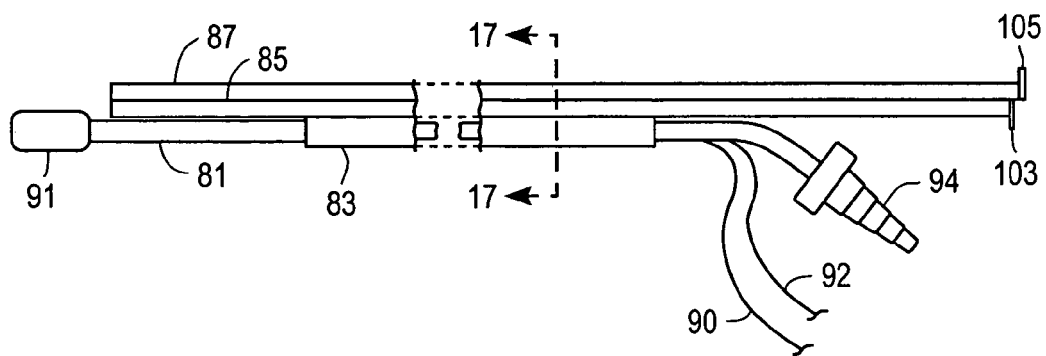
FIG. 15 is a partial plan view of a releasable guide in accordance with the embodiment illustrated in FIG. 10.
Figure 16:
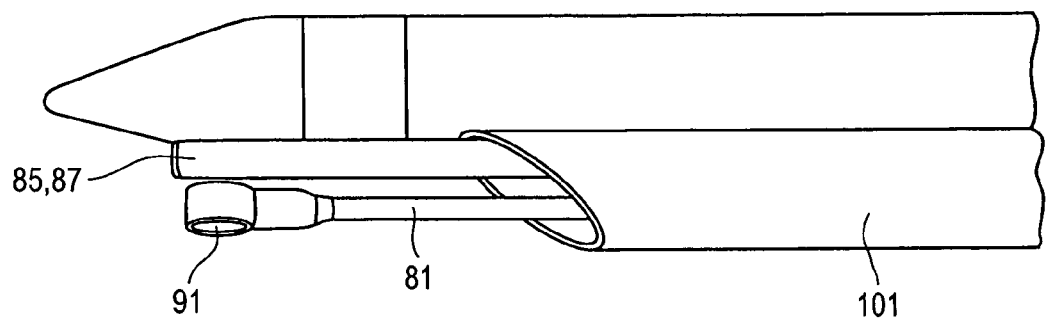
FIG. 16 is a partial plan view of the releasable guide of FIG. 10 assembled within an endoscopic cannula.
Figure 17:
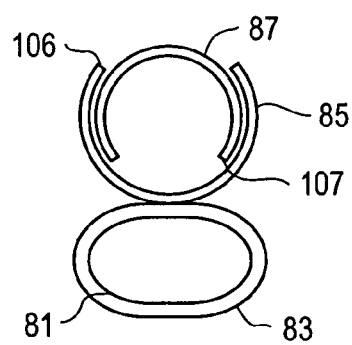
FIG. 17 is a sectional view of the releasable guide of FIG. 15.
Figure 18:
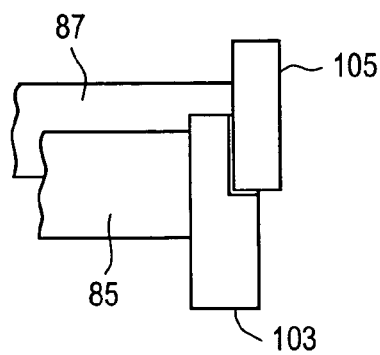
FIG. 18 is a partial plan view of one embodiment of the proximal end of the guide channel of the releasable guide of FIG. 15.
Figure 19:
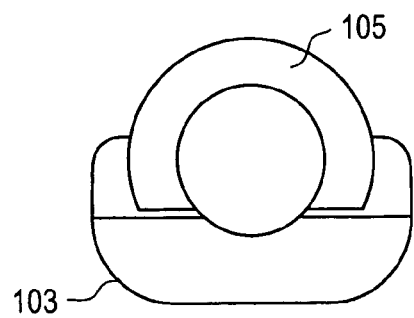
FIG. 19 is an end view of the proximal end of the guide channel of FIG. 15.

Referring now to the partial plan view of FIG. 16 and the sectional view of FIG. 17, there is shown a non-round guide tube 83 that is attached to the lower segment 85 of the guide channel and that slidably supports therein the suction tube 81 of corresponding non-round cross section. In this way, the guide channel formed by segments 85, 87 is retained in substantially parallel axial alignment with the suction tube 81 as the suction pod 91 and the distal end of the guide channel are relatively slidably positioned near and against the epicardium of a patient's heart. In addition, as illustrated in the partial sectional view of FIG. 17, the assembly of guide tube 83 and suction tube 81 and guide channel 85, 87 may all be disposed within the instrument channel of an endoscopic cannula 101 having a distal end disposed to facilitate endoscopic viewing of the suction pod 91 and the distal end of the guide channel 85, 87. Also, the upper and lower segment 85, 87 of the guide channel may include stepped flanges 103, 105 at the proximal ends thereof, as illustrated in FIGS. 15, 18 and 19, to facilitate positive orientation of the upper and lower segments 85, 87 in the closed configuration until the upper segment 87 is slid proximally, or slid proximally and rotated, relative to the lower segment 85 in order to re-configure the guide channel in the alternate configuration of an elongated open slot along the entire length thereof. As shown in the sectional view of FIG. 17, the upper 87 segment can be rotated in the lower segment 85 from the closed configuration in order to align the respective elongated slots sufficiently to release a cardiac lead 89 from within the guide channel.

Figure 20:
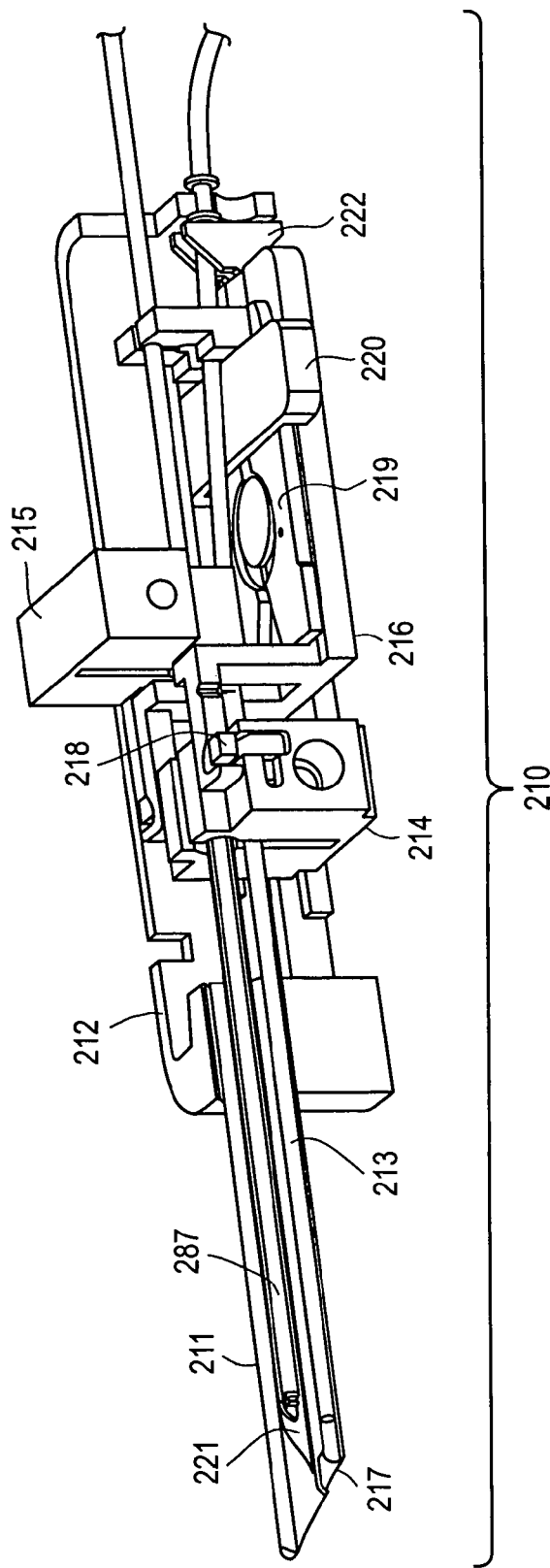
FIG. 20 is a perspective cut away view of a cardiac lead delivery device in accordance with one embodiment of the present invention.
Figure 22A:
FIGS. 22a, b, c and d are, respectively, top, side, end and bottom views of an U-shaped body in accordance with one embodiment of the present invention.
Figure 22B:
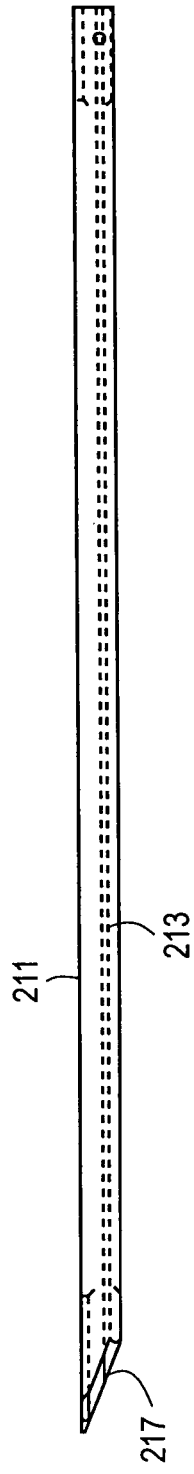
Figure 22C:
Figure 22D:
Figure 25:
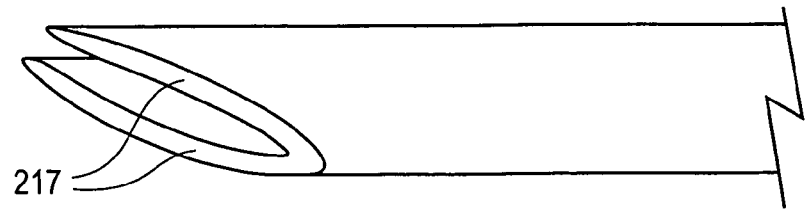
FIG. 25 is a partial plan view of another embodiment of the suction port in accordance with one embodiment of the present invention.
Figure 26:
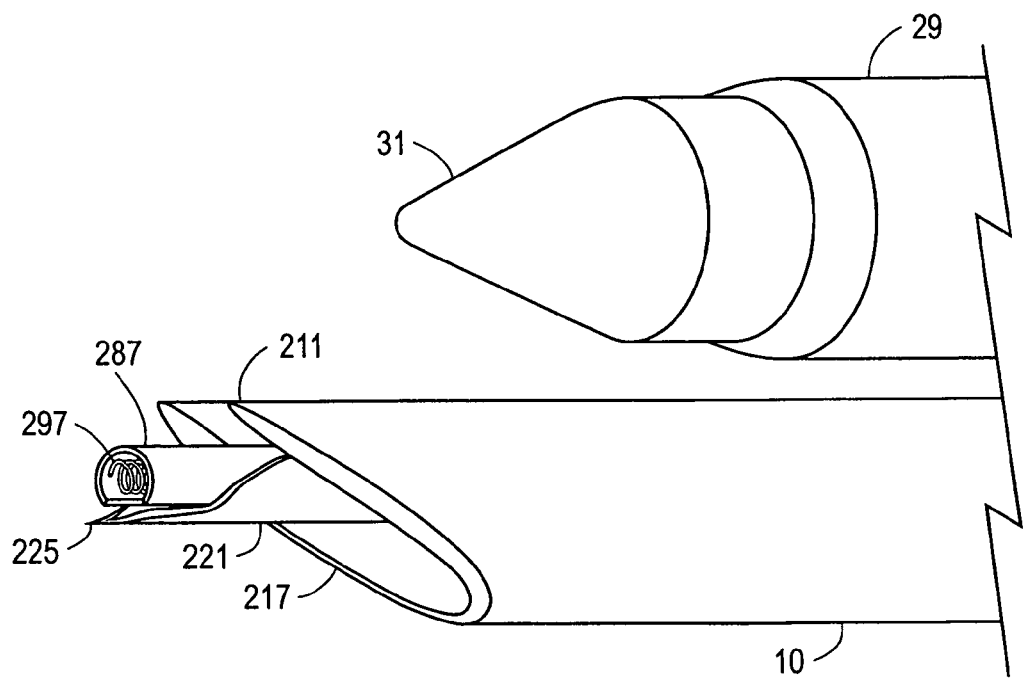
FIG. 26 is a partial side view of the cardiac lead delivery device of FIGS. 20 with a guide channel encasing a cardiac lead advanced in accordance with one embodiment of the present invention.

Referring now to FIG. 20, there is shown another embodiment of a cardiac lead delivery device 210 according to the present invention. The cardiac lead delivery device 210 includes a housing 212. An U-shaped elongated body 211 is attached to the distal end of the housing 212. Referring to FIGS. 22a-d, the U-shaped elongated body 211 can be hollow and includes a suitable hose connection 213 for connection to a vacuum source at the proximal end, and the distal end of the U-shaped body 211 may be angled relative to the elongated axis of the body 211, as shown the angled distal end of the U-shaped body 211 includes a U-shaped suction that is confined within boundary walls disposed substantially in a plane that is skewed at an acute angle relative to an elongated axis of the cardiac lead delivery device 210. An upward orientation of the U-shaped body 211 is preferred for better visualization of a cardiac lead that is disposed within the U-shape during placement. In addition, the suction port 217 may comprise two separate channels as illustrated in FIG. 25 that are positioned on opposite sides of the distal end of the elongated body 211.

The suction port 217 at the distal end of the U-shaped body 211 can be positioned against the epicardium to facilitate temporary fixation thereto resulting from reduced air pressure of vacuum supplied to the hose 213. The distal end of the U-shaped body may thus be held in accurate temporary fixation in alignment with a selected surgical site on the epicardium relative to the suction fixation location of the suction port 217 on the epicardium. The angled suction port 217 may also be used to apply gentle pressure on the epicardium to stop bleeding at small puncture sites in the epicardium.

The U-shaped body 211 is sized to accommodate slidable movement therein of a hollow needle 221 that is connected a bulkhead 214 located inside the housing 212. Referring to FIGS. 23a-d, the needle 221 may exhibit lateral flexibility over its length at the proximal end to the sharpened distal end 225. When used to place pacing or defibrillating leads, the needle 221 may be about 2-3 mm in diameter with an internal bore of sufficient size to accommodate a lead and guide channel of diameter up to approximately 2 mm in diameter. It should be noted that the cardiac lead delivery device 210 is sized to fit in slidable orientation within the instrument channel 28 of about 5-10 mm diameter in the endoscopic cannula 27, as illustrated in FIG. 2.

Referring now to the cut away partial plan view of FIG. 21, there is shown an assembly of suction port 217 of the cardiac lead delivery device 210 in which a needle 221 is slidably disposed within the U-shaped body 211. The guide channel 287 is slidably and rotatably received within the needle 221 and a cardiac pacing or defibrillating lead 289 is housed within the guide channel 287.

Figure 27A:
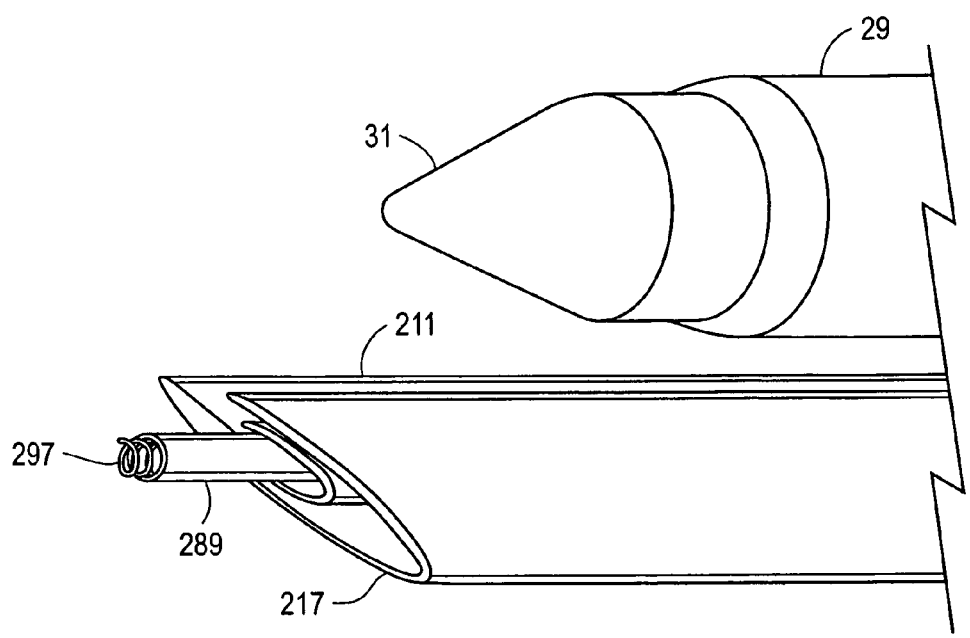
FIGS. 27A and 27B are, respectively, partial plan and perspective views of the distal end of the releasable guide in accordance with one embodiment of the present invention.
Figure 27B:
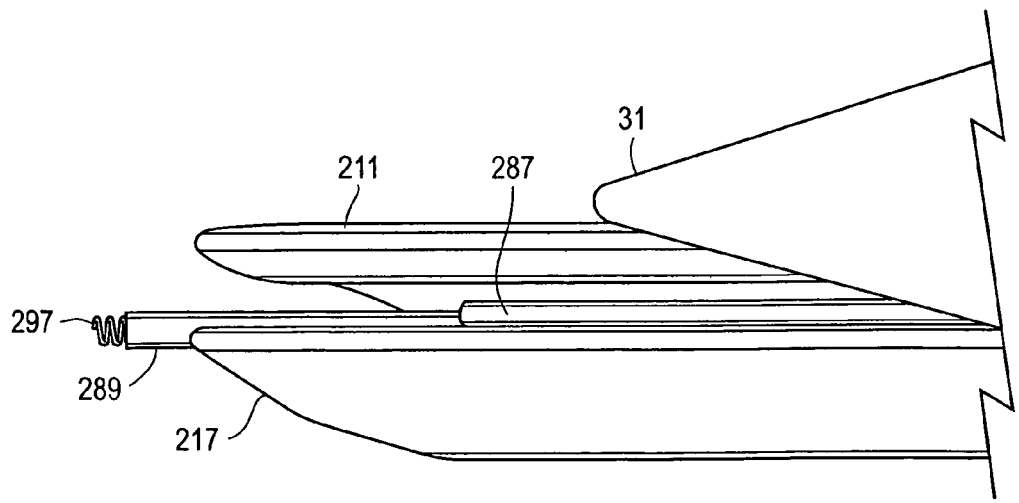

The guide channel 287 is coupled to an actuation arm 215, as illustrated in FIG. 20, that is slidable along the housing 212. The cardiac pacing or defibrillating lead 289 is slidably and rotatably housed within the guide channel 287 in the closed configuration, and includes a helical or screw-in electrode 297 attached to the distal end of the cardiac lead 289, as illustrated in FIGS. 27A and 27B. The suction port 217 facilitates the temporary suction attachment while the electrode 297 at the distal end of the cardiac lead 289 that is slidably guided within the guide channel 287 (which is disposed in substantially fixed axial orientation relative to the suction port 217) is being anchored into myocardium.

Figure 28:
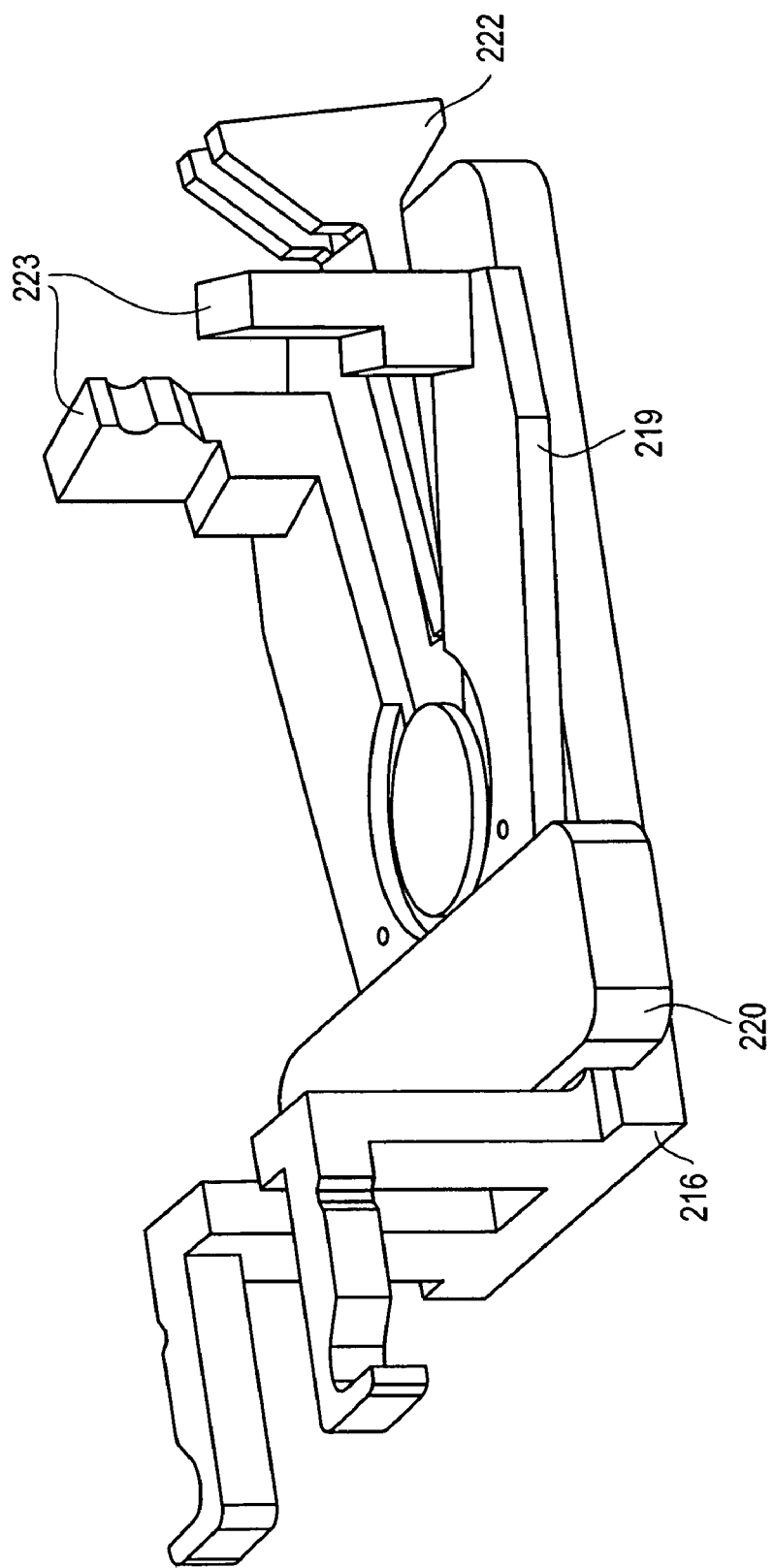
FIG. 28 is a perspective view of an open clamp according to one embodiment of the present invention.
Figure 29:
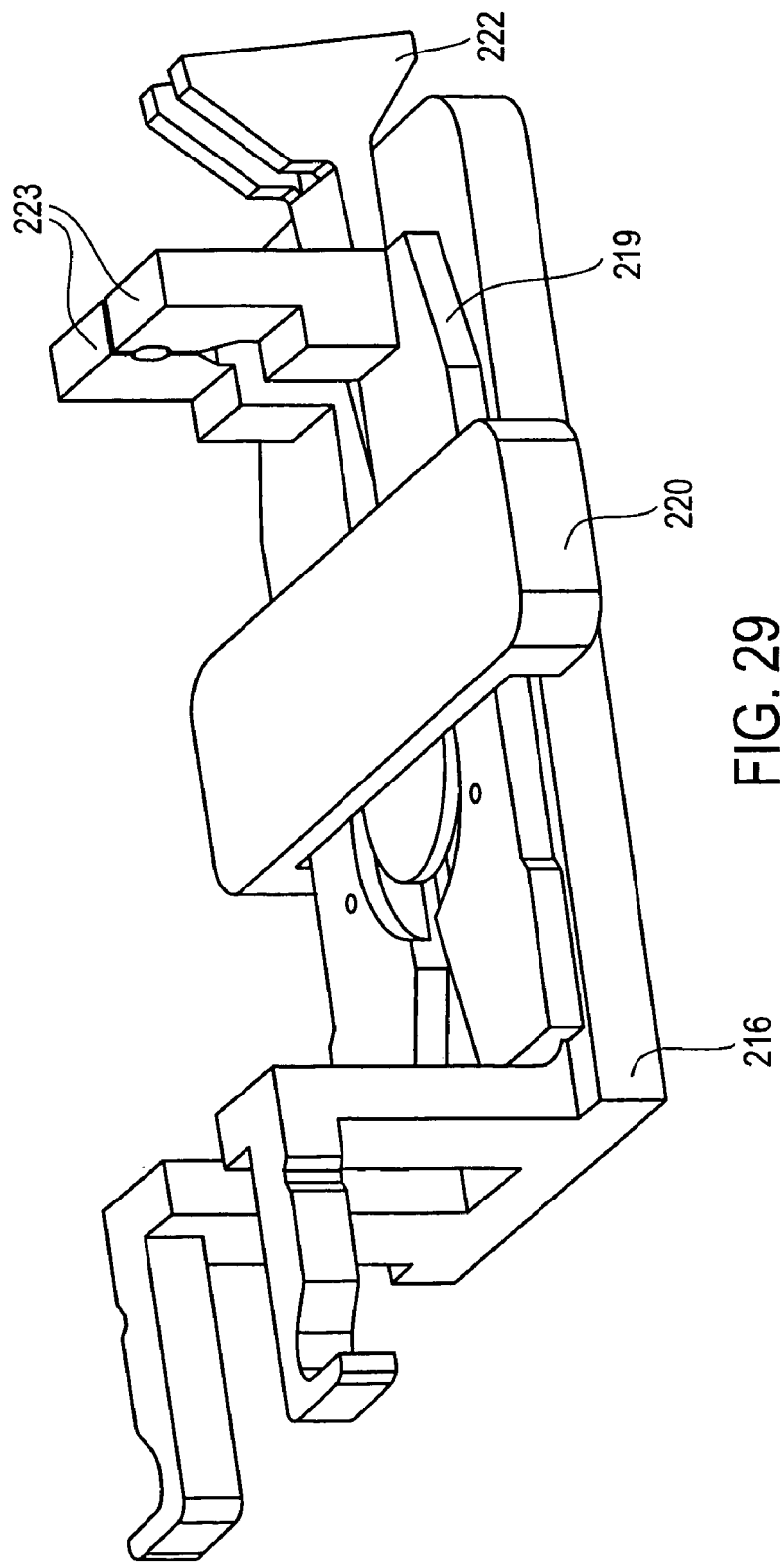
FIG. 29 is a perspective view of the clamp of FIG. 28 disposed in another operational configuration according to one embodiment of the present invention.
Figure 30:
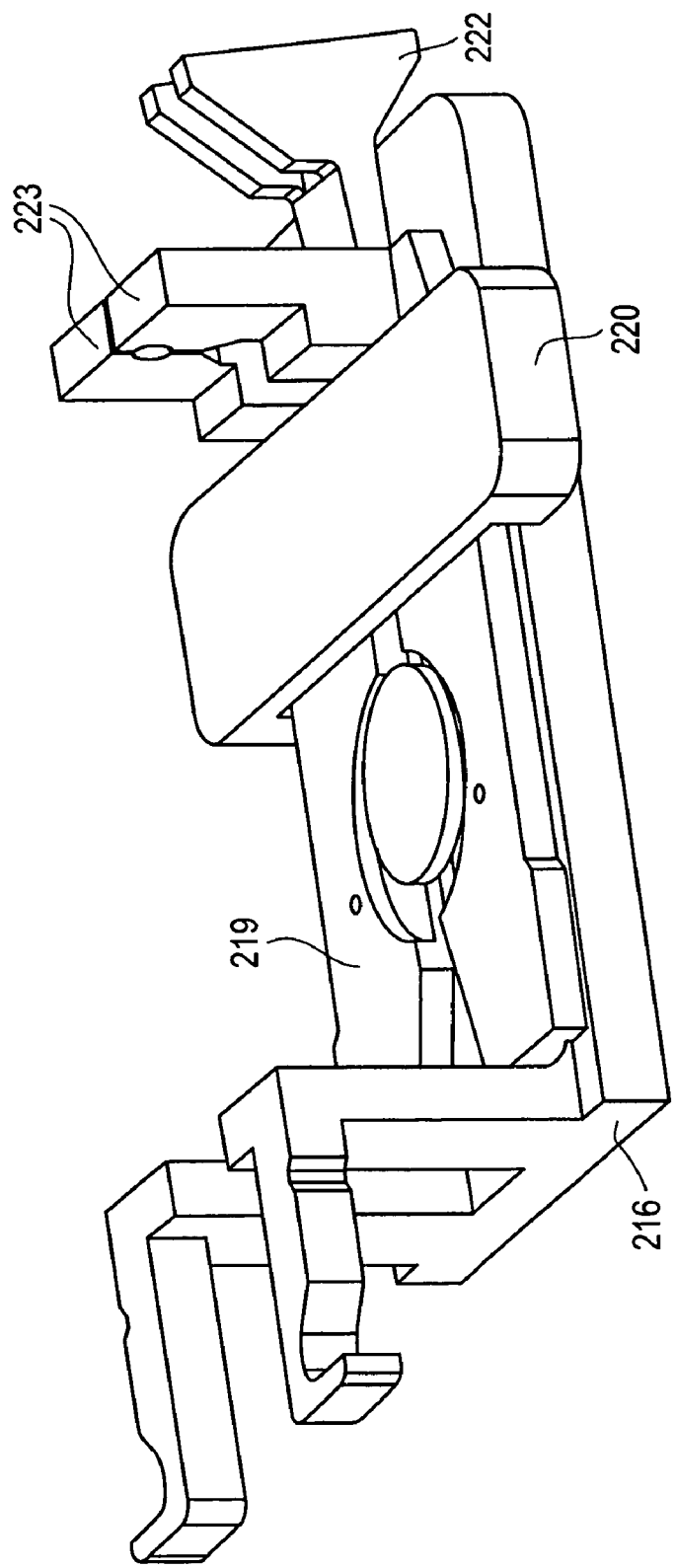
FIG. 30 is a perspective view of the clamp of FIG. 28 disposed in another operational configuration according to one embodiment of the present invention.

A sled 216, as illustrated in FIGS. 20, 28-35, is located proximally of the bulkhead 214 and is slidable within the housing 212. In one embodiment, the sled 216 is temporarily referenced against the bulkhead 214 by a pair of resilient detents 218. Clamp 219 with arms 223 is pivotally mounted on sled 216 for activation between opened and clamped configurations by a slide 220. The clamp 219 is open when the slide 220 is positioned near the distal end of the sled 216 as illustrated in FIG. 28. The cardiac lead 289 is placed between the two clamp arms 223 and within the guide channel 287 that is positioned within the needle 221. When the slide 220 is positioned midway on the sled 216 as illustrated in FIG. 29, the cardiac lead 289 is loosely clamped in place for easier maneuverability. When the slide 220 is positioned against the clamp arms 223 and at the proximal end of the sled 216, the clamp 219 is fully engaged and the cardiac lead 289 is firmly clamped within the clamp arms 223, as illustrated in FIG. 30.

The suction hose 213 is disposed above the slide 220 and located within the U-shaped body 211. In one embodiment, a wedge 222 holds the suction 213 out of the way of the cardiac lead 289. In another embodiment, the suction hose 213 exits the housing 212 distal the bulkhead 214.

Figure 24:
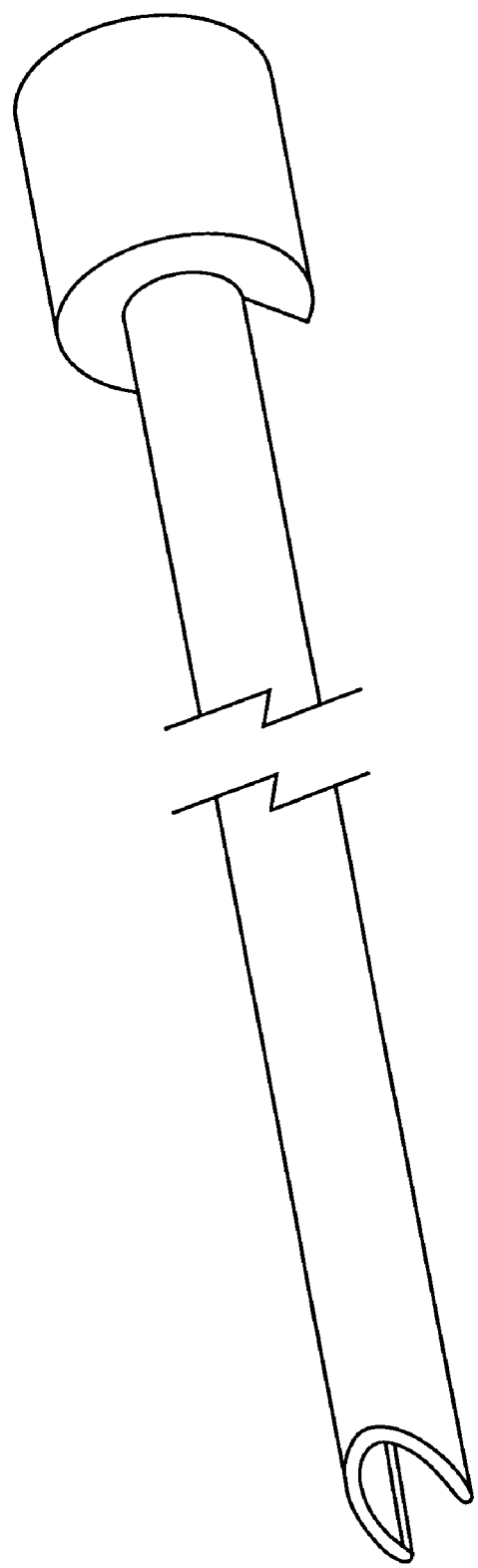
FIG. 24 is a perspective view of a guide channel in accordance with one embodiment of the present invention.

Referring now to FIG. 31, after the cardiac lead 289 is secured within the clamp arms 223 of clamp 219, the actuation arm 215 is moved distally forward to abut the bulkhead 214 which in turns moves distally forward advancing the needle 221 that is attached to the bulkhead 214. Next, as shown in FIG. 32, the actuation arm 215 moves further distally, causing the sled 216 and the guide channel 287 to move forward which in turn causes the cardiac lead 289 to slide along the needle 221 into the heart. In another embodiment, moving the actuation arm 215 distally causes the sled 216 to bump against the detents 218 creating a friction stop. The guide channel 287 may be angled distally, as illustrated in FIG. 24, to move heart tissue away from the incision caused by the needle 221.

Figure 33:
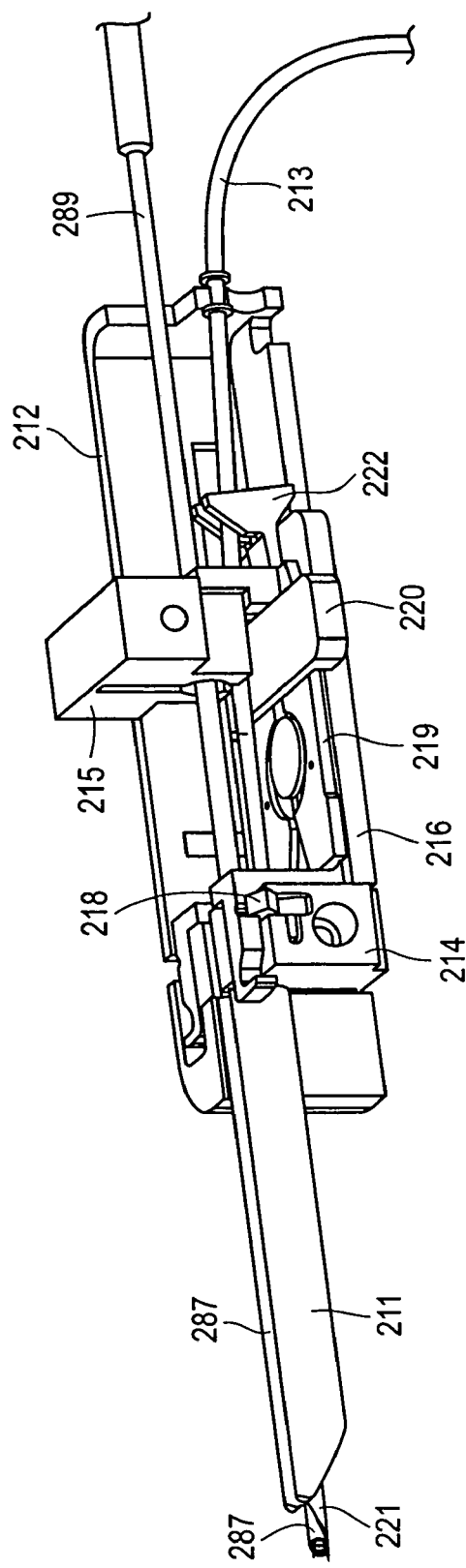
FIG. 33 is a cut-away perspective view of the cardiac lead delivery device of FIG. 32 with a guide channel slightly withdrawn in accordance with one embodiment of the present invention.
Figure 34:
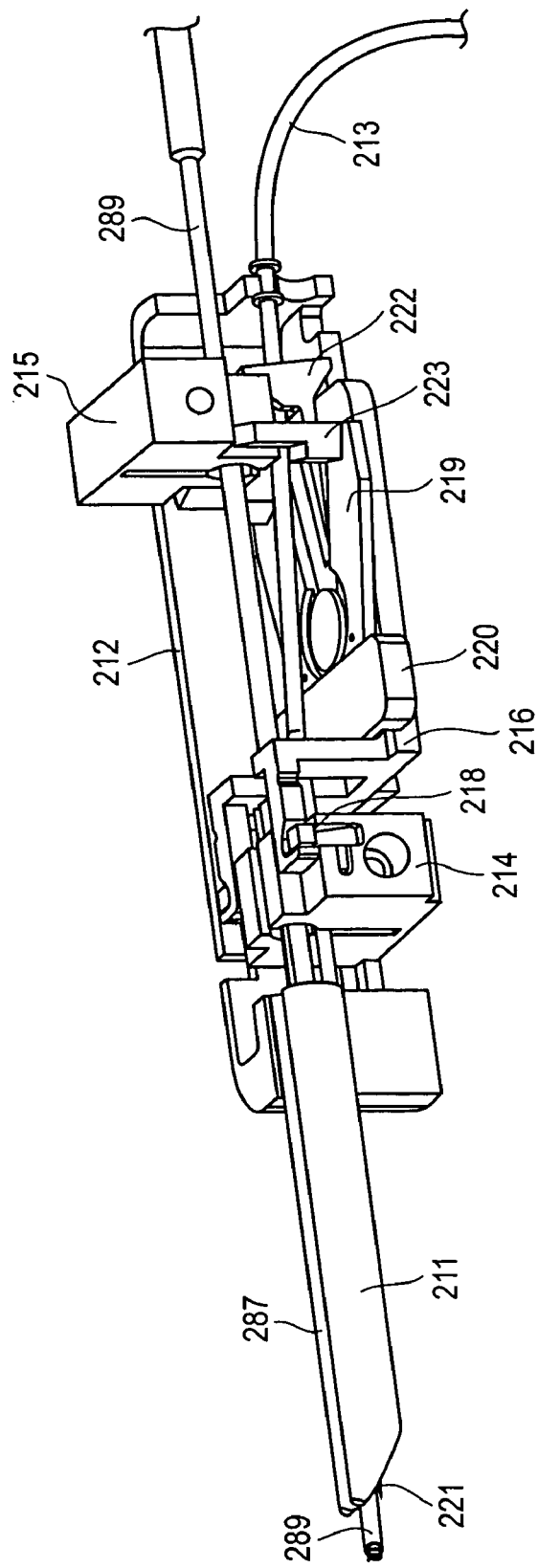
FIG. 34 is a cut-away perspective view of the cardiac lead delivery device of FIG. 32 with the clamp unclamped and a needle withdrawn from a heart incision in accordance with one embodiment of the present invention.
Figure 35:
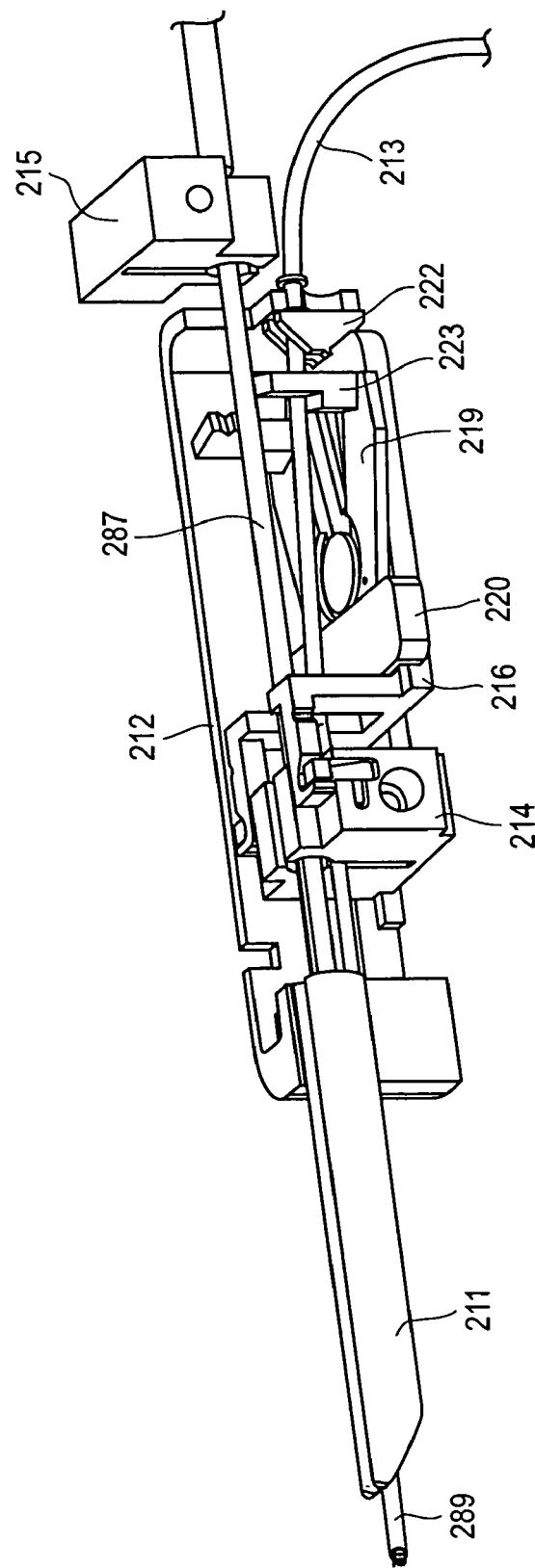
FIG. 35 is a cut-away perspective view of the cardiac lead delivery device of FIG. 32 with the guide channel completely withdrawn in accordance with one embodiment of the present invention.

After the electrode 297 on the distal end of the cardiac lead 289 is positioned into the myocardium of a patient's beating heart, the actuation arm 215 is pulled proximally to abut against the clamp arms 223, as illustrated in FIG. 33. These movements of the actuation arm 215 results in the guide channel 287 being withdrawn slightly through the U-shaped body 211 to provide better endoscopic visualization of the placement of the distal end of a cardiac lead in a patient's heart. The cardiac electrode 297 is rotated and anchored by hand into the correct position. The slide 220 is then moved distally to unclamp the cardiac electrode 297 from the clamp 219. The electrode 296 remains anchored in the patient's heart as the actuation arm 215, coupled with the guide channel 287, is completely withdrawn from the housing 212 at the same time that the bulkhead 214 is moved proximally within the house to remove the needle 221 from the heart incision, as shown in FIGS. 34 and 35.

The placement of the suction port 217 at the distal end of the lead placement assembly facilitates establishing temporary vacuum-assisted attachment of the suction port 217 to the epicardium (or to myocardium that is exposed via the entry under the pericardium) which can then be depressed or otherwise distorted by manual application of axial or lateral force at the proximal end of the instrument in order to position the electrode 297 at the proper location and angle for anchoring in the myocardium of the patient's beating heart.

Figure 36:
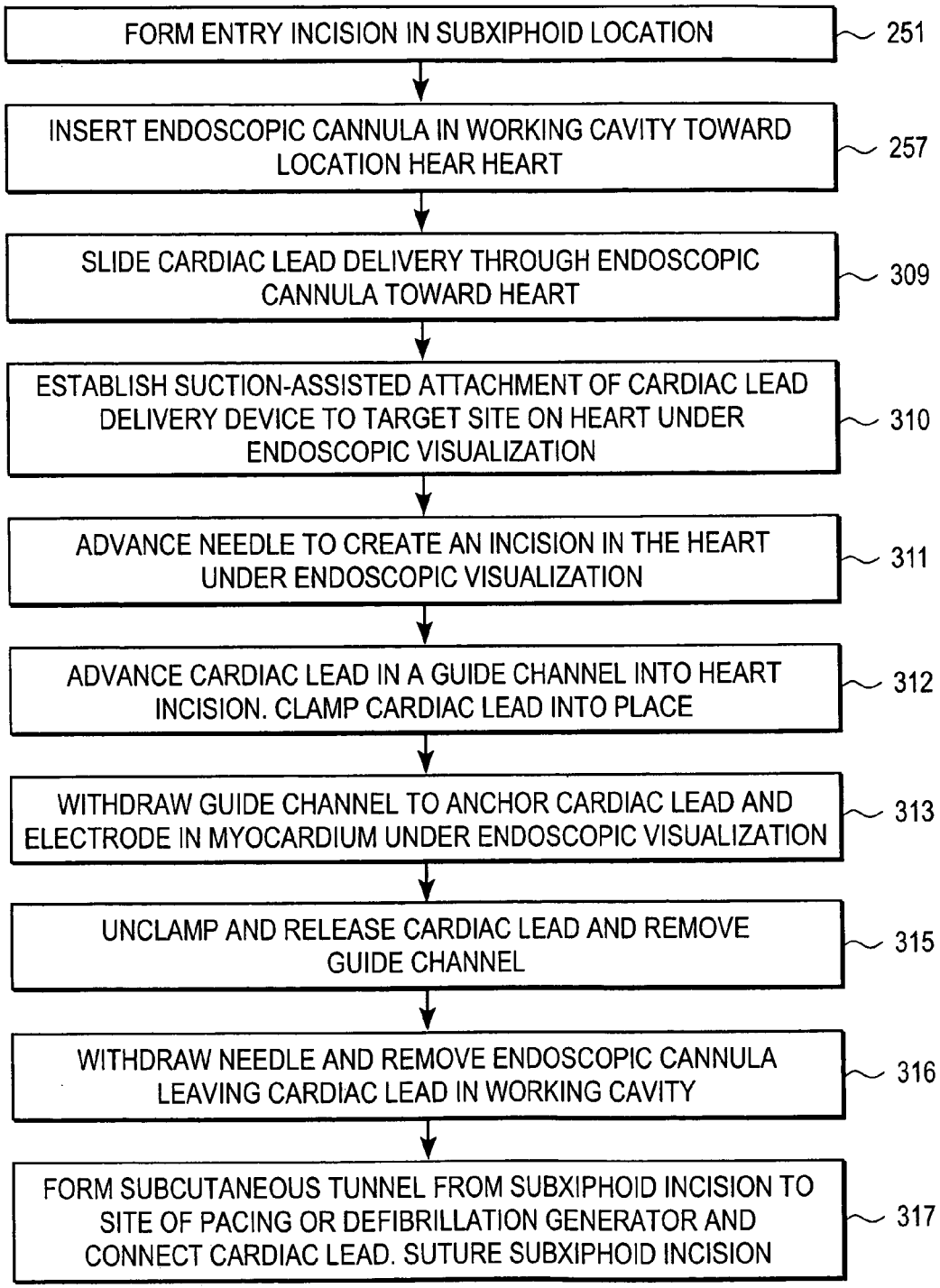
FIG. 36 is a flow chart illustrating a surgical procedure for implanting a cardiac lead in accordance with one embodiment of the present invention.

In operation, as illustrated in the flow chart of FIG. 36, the initial surgical procedures are performed in a manner as previously described in the aforecited related applications from the initial incision 251 through to the insertion of the endoscopic cannula 257. Thereafter, the releasable guide assembly, including U-shaped body 211, needle 221 and guide channel 287, is slid through the endoscopic cannula 309 toward the heart. The suction port 217 is advanced into contact with the myocardium through the penetrated pericardium and suction is established to temporarily anchor 310 the suction port 217 at a desired surgical site. A cardiac lead 289 with a screw-in electrode 297 on the distal end of the cardiac lead is positioned at or near the distal end of the guide channel 287 in the closed configuration as the guide channel is advanced 312 toward the desired surgical site adjacent the temporary anchor site of the suction channel 211 on the myocardium. The guide channel is withdrawn slightly to provide endoscopic visualization of the cardiac lead in the heart incision. The proximal end of the cardiac lead 289 may now be manually manipulated to screw in the electrode 297 at the distal end into the myocardium to thereby anchor 313 the cardiac lead 289 in the myocardium.

The guide channel 287 may now be completely withdrawn from the patient's body. Thereafter, the assembly of U-shaped body 211 and needle 221 may be retracted from the instrument channel of the cannula 27, and the endoscopic cannula 27 may be removed 316 from within the working cavity, with the cardiac lead 289 in position therein. A subcutaneous tract is formed from the subxiphoid incision to the location of the pacing or defibrillation generator, usually placed in the patient's upper chest, and the cardiac lead is then connected to the generator 317. The subxiphoid (or other) incision is sutured closed to complete the surgical procedure. Of course, the surgical procedures described above including steps 309-315 may be performed multiple times in order to anchor multiple cardiac leads in the myocardium prior to removing 316 the endoscopic cannula and suturing 318 the initial incision closed.

Therefore the surgical apparatus and methods of the present invention promote careful placement of surface electrodes on the epicardial surface for electrocardial mapping of a beating heart. In addition, the present invention promotes careful placement of a needle or electrode or other surgical instrument on the surface of a beating heart by temporarily affixing the distal end of a guiding cannula at a selected position on the heart in response to suction applied to a suction port in a structure that supports the surface electrodes. The guiding cannula can be positioned through a working cavity formed in tissue between the heart and a subxiphoid or other entry incision to minimize trauma and greatly facilitate surgical treatment of a beating heart. Such treatments and procedures include initial sensing of electrical signals or delivery of pacing signals at selected sites on the epicardium for analyzing optimum sites at which cardiac electrodes are anchored for supplying electrical pacing signals with maximum therapeutic benefit, and thereafter placing pacing or defibrillating leads into the myocardium at the optimum sites.

What is claimed is:

1. Apparatus for performing a surgical procedure on the heart of a patient through a working cavity in tissue between the heart and an entry incision, the apparatus comprising:
    a cannula configured for passing extravascularly through the entry incision and working cavity toward the heart;
    a suction attachment supported by the cannula and configured for contacting an exterior target site on the heart; and
    a support channel for a cardiac lead that is disposed on the suction attachment and that includes coaxial mating segments that are relatively rotatable about a coaxial axis thereof, each segment having a longitudinal slot extending along the entire length of an outer wall between distal and proximal ends of the segment for selective configuration as a closed channel in one relative rotational orientation for confining a cardiac lead in the support channel or as a channel open longitudinally along the entire length of the outer wall between proximal and distal ends of the segment in another relative rotational orientation of the segments that aligns the longitudinal slots for releasing a cardiac lead laterally from within the entire length of the support channel through the aligned slots.

2. Apparatus according to claim 1 including a cardiac lead connected to an electrode disposed near a surface of the suction attachment to contact the heart externally, the cardiac lead extending along the support channel in the closed configuration to the proximal ends of the segments for connecting the electrode to a utilization circuit and being releasable laterally from the support channel through the longitudinal slots formed in the segments as rotationally oriented in the open configuration.

* * * * *

UNITED STATES PATENT AND TRADEMARK OFFICE
CERTIFICATE OF CORRECTION

PATENT NO.         : 7,526,342 B2
APPLICATION NO. : 10/697906
DATED              : April 28, 2009
INVENTOR(S)       : Albert K. Chin, John W. Davis and Randy W. Westlund It is certified that error appears in the above-identified patent and that said Letters Patent is hereby corrected as shown below:

Title page 2, under References Cited, patent number 3,338,916 should be 3,336,916.

Signed and Sealed this

Tenth Day of November, 2009

David J. Kappos
*Director of the United States Patent and Trademark Office*